United States Patent
Dubberstein et al.

[11] Patent Number: 6,159,153
[45] Date of Patent: Dec. 12, 2000

[54] METHODS AND SYSTEMS FOR ULTRASOUND SCANNING USING SPATIALLY AND SPECTRALLY SEPARATED TRANSMIT ULTRASOUND BEAMS

[75] Inventors: David T. Dubberstein, Hales Corners, Wis.; Olaf T. von Ramm, Efland, N.C.

[73] Assignee: Duke University, Durham, N.C.

[21] Appl. No.: 09/224,746

[22] Filed: Dec. 31, 1998

[51] Int. Cl.[7] ............................................. A61B 8/00
[52] U.S. Cl. ........................................ 600/443; 128/916
[58] Field of Search ........................ 600/437, 440–443, 600/447; 73/625–626, 599

[56] References Cited

U.S. PATENT DOCUMENTS

| | | | |
|---|---|---|---|
| Re. 35,148 | 1/1996 | Lizzi et al. | 600/442 |
| 4,413,520 | 11/1983 | Murakami et al. | 73/609 |
| 4,549,533 | 10/1985 | Cain et al. | 600/447 |
| 4,569,231 | 2/1986 | Carnes et al. | 73/626 |
| 4,798,210 | 1/1989 | Ledley | 600/437 |
| 4,815,043 | 3/1989 | Shirasaka | 367/7 |
| 4,855,961 | 8/1989 | Jaffe et al. | 367/7 |
| 4,893,283 | 1/1990 | Pesque | 600/447 |
| 5,301,674 | 4/1994 | Erikson et al. | 600/447 |
| 5,360,007 | 11/1994 | Shinomura et al. | 600/447 |
| 5,361,767 | 11/1994 | Yukov | 600/442 |
| 5,549,111 | 8/1996 | Wright et al. | 600/443 |
| 5,601,086 | 2/1997 | Pretlow, III et al. | 600/458 |
| 5,617,863 | 4/1997 | Roundhill et al. | 600/447 |
| 5,793,701 | 8/1998 | Wright et al. | 367/7 |
| 5,891,037 | 4/1999 | Hossock et al. | 600/443 |
| 5,891,038 | 4/1999 | Seyed-Bolorforesh et al. | 600/447 |
| 5,902,242 | 5/1999 | Ustuner et al. | 600/443 |
| 5,993,393 | 11/1999 | Ryan et al. | 600/447 |

OTHER PUBLICATIONS

Mallart et al., "Improved Imaging Rate Through Simultaneous Transmission of Several Ultrasound Beams," SPIE, 1733, pp. 120–130, p. 29.

*Primary Examiner*—Francis J. Jaworski
*Attorney, Agent, or Firm*—Myers Bigel Sibley & Sajovec

[57] ABSTRACT

Multiple transmit ultrasound beams are generated by an ultrasound transducer at different frequencies in different directions in a region of a body during a maximum scan range interval. Transmitting multiple transmit ultrasound beams during the maximum scan range interval may provide an increase in the data acquisition rate compared to conventional ultrasound imaging systems. The transmit ultrasound beams are tracked using parallel receive processing and filtered to provide ultrasound scan lines for display. The respective directions of the transmit ultrasound beams are selected to define a separation angle therebetween which may reduce interference between the transmit ultrasound beams. The maximum scan range interval includes a time interval from a first start time to a second start time which is less than a total time for one of the transmit ultrasound beams to propagate to a maximum scan range in the region and a corresponding reflected transmit ultrasound beam to propagate from the maximum scan range to the ultrasound transducer. The ultrasound scan lines are displayed using a line-by-line frequency interlace pattern which may reduce the effect of frequency dependent attenuation in the region. The line-by-line frequency interlacing may also reduce a difference in speckle size due to the different frequencies.

28 Claims, 14 Drawing Sheets

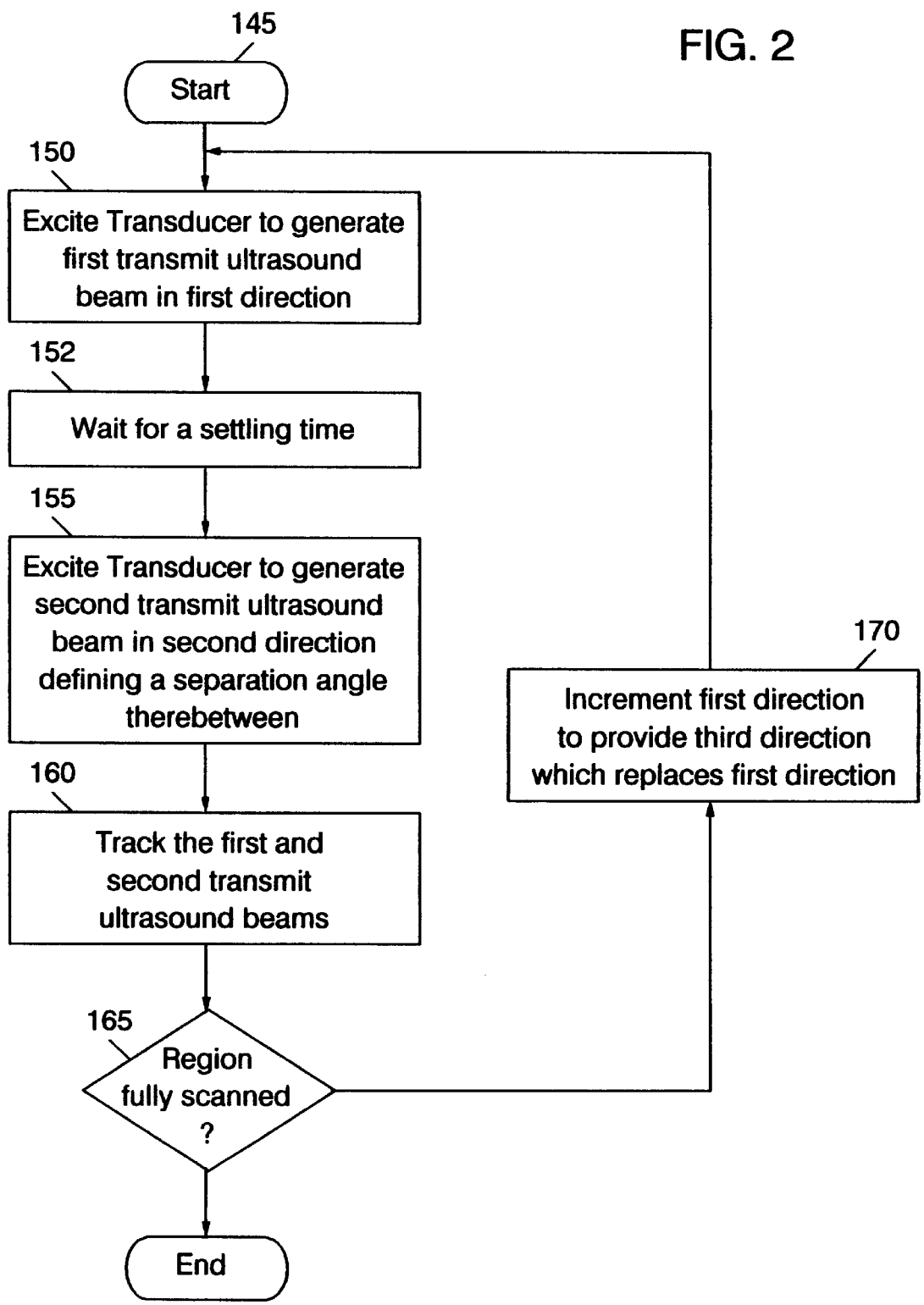

METHODS AND SYSTEMS FOR ULTRASOUND SCANNING USING SPATIALLY AND SPECTRALLY SEPARATED TRANSMIT ULTRASOUND BEAMS

This invention was made with Government support under grant number CDR 8622201 from The National Science Foundation. The Government has certain rights to this invention.

FIELD OF THE INVENTION

The present invention relates to the field of imaging in general and more particularly to ultrasound imaging.

BACKGROUND OF THE INVENTION

The heart is an intricately shaped, moving, three dimensional organ. Volumetric ultrasound imaging may generate images of the heart which may not be attainable with a two-dimensional ultrasound scanner. One of the challenges in generating volumetric ultrasound images is the high data acquisition rate which may be needed to scan the heart at a desired frame rate such as 30 frames per second (in real time).

In particular, ultrasound imaging may provide images of tissue in a body region by exciting an ultrasound transducer that generates ultrasound energy directed into the tissue. The ultrasound transducer, such as a piezoelectric crystal, may be excited with an electrical signal that produces a pressure wave which propagates into the tissue. As the propagating pressure wave encounters changes in the acoustic impedance of the tissue, a portion of the pressure wave is reflected back towards the ultrasound transducer which converts the reflected pressure wave back into an electrical signal for processing and display as part of an ultrasound image.

An ultrasound image of the tissue may be generated by electronically steering the pressure waves in the region by controlling the phasing of the excitations to a plurality of ultrasound transducer elements to form a transmit ultrasound beam. For example, electronic steering of transmit ultrasounds beams is discussed in U.S. Pat. No. 4,596,145 to Smith et al. In general, each excited ultrasound transducer element produces a corresponding pressure wave that is timed to constructively combine with pressure waves generated by other ultrasound transducer elements at a predetermined angle and range in the tissue. Consequently, phasing of the excitations to the plurality of ultrasound transducer elements may enable the transmit ultrasound beam to be steered within the region without moving the ultrasound transducer.

A number of the ultrasound transducer elements operate in a receive mode which receive the reflected pressure waves created by the corresponding transmit ultrasound beams and convert the pressure waves to electrical signals. The ultrasound system then adjusts the timing of the electrical signals that correspond to the reflected pressure wave to generate a receive ultrasound beam. Moreover, the ultrasound system processes (or focuses on) each reflected pressure wave dynamically (known as dynamic focusing). In particular, pressure waves reflected from points in the tissue located closer to the ultrasound transducer are reflected back and arrive at the ultrasound transducer earlier than points that are farther away from the ultrasound transducer.

Using dynamic focusing, the ultrasound system processes the earlier reflected pressure waves by focusing on the closer points first and then focusing on the farther points as time elapses. Thus the ultrasound system forms a receive ultrasound beam that corresponds to a transmit ultrasound beam by dynamically focusing on the reflected pressure waves created by the corresponding transmit ultrasound beam as the transmit ultrasound beam propagates in the tissue.

It is known to use parallel receive processing in conjunction with dynamic focusing to increase the data acquisition rate of the ultrasound imaging system. For example, parallel receive processing is discussed in U.S. Pat. No. 4,694,434 to von Ramm. In general, parallel receive processing may be performed in two stages. First, a broadened transmit beam is propagated into the tissue. The transmit ultrasound beam may be broadened by using a plurality of the ultrasound transducer elements adjacent to one another in the center of the ultrasound transducer as the transmitting elements. A broadened transmit ultrasound beam may insonify a larger amount of tissue in the body region. Second, parallel receive ultrasound beams are simultaneously acquired around the broadened transmit ultrasound beam.

Increasing the number of parallel receive ultrasound beams may, however, cause some of the receive ultrasound beams to under-steer the desired location. For example, broadening the transmit ultrasound beam may cause a decrease in the acoustic Signal-to-Noise Ratio (SNR) and a loss of resolution, thereby possibly degrading the image quality. The under-steer may be exacerbated as the receive ultrasound beams are placed farther from the center of the broadened transmit ultrasound beam. The under-steer may limit conventional volumetric ultrasound imaging systems to acquiring 16 parallel receive ultrasound beams around a single broadened transmit ultrasound beam.

It is known that improvements in the quality of ultrasound imaging may be achieved by increasing the frequency at which the ultrasound transducers described above are excited. For example, an ultrasound transducer array that is excited at 5.0 MHz may provide better image quality than an ultrasound transducer array that is excited at 2.5 MHz. Scanning a region using the higher frequency may, however, require more transmit ultrasound beams.

In particular, the frequency of the excitation may be proportional to the resolution of a scan so that, as the frequency increases, the resolution of the scan increases. Increasing the resolution of the scan may cause the spacing between adjacent transmit ultrasound beams decrease so that more transmit ultrasound beams may be needed to adequately scan the region. For example, conventional ultrasound systems using 2.5 MHz excitation may provide a lateral resolution of about 1°. Increasing the frequency above 2.5 MHz may increase the resolution to less than 1°. Consequently, the data acquisition rate of an ultrasound imaging system that generates transmitted ultrasound beams above 2.5 MHz may need to be increased to maintain adequate scanning.

The data acquisition rate of conventional ultrasound imaging systems may also define the size of the region that can be imaged in real time. In particular, increasing the data acquisition rate may allow the size of the imaged region to be increased while maintaining a desired frame rate. For example, increasing the data acquisition rate may allow an increase in a volume scan angle from 60° to 80° to enable the display of the four heart chambers in the apical view. Alternatively, increasing the data acquisition rate may be used to provide deeper scans while maintaining a desired frame rate. Accordingly, there continues to exist a need to further increase the data acquisition rate of ultrasound imaging systems.

SUMMARY OF THE INVENTION

It is, therefore, an object of the present invention provide for improved ultrasound imaging systems.

It is a further object of the present invention to allow an increase in the data acquisition rate for ultrasound imaging systems.

It is a further object of the present invention to allow an improvement in the image quality of images generated by ultrasound imaging systems.

These and other objects of the present invention may be provided by generating a plurality of ultrasound beams in a plurality of directions, wherein at least two of the ultrasound beams are generated at different frequencies. Generating a plurality of ultrasound beams in a plurality of directions may provide an increase in the data acquisition rate of the ultrasound imaging system. Using more than one frequency may allow the respective reflected pressure waves created by the plurality of transmit ultrasound beams to be separated more easily, thereby reducing the interference between the plurality of transmit ultrasound beams.

In particular, the plurality of transmit ultrasound beams are transmitted in a time interval which is less than a maximum scan range interval. The maximum scan range interval is equal to the time needed for a transmit ultrasound beam to propagate from an ultrasound transducer to a maximum scan range plus the time needed for a corresponding reflected pressure wave to propagate from the maximum scan range to the ultrasound transducer. The plurality of transmit ultrasound beams transmitted in the maximum scan range interval may provide an increase in the data acquisition rate compared to conventional ultrasound imaging systems by reducing time needed to scan the region. According to conventional ultrasound imaging systems, only one ultrasound beam is transmitted during the maximum scan range interval.

In one embodiment, a first ultrasound beam is generated at a first frequency in a first direction and a second ultrasound beam is generated at a second frequency in a second direction, wherein the direction of the first transit ultrasound beam and the direction of the second transmit ultrasound beam define a separation angle therebetween. The separation angle may reduce the interference between the first and second ultrasound beams generated during the maximum scan range interval.

In a further aspect of the present invention, a plurality of ultrasound beams are transmitted in a plurality of directions, wherein at least two of the ultrasound beams are generated at different frequencies in a sector of the region. Sectors of the region may thereby be scanned using transmit ultrasound beams that have alternating frequencies. Alternating the frequency of the transmit ultrasound beams in a sector of the region may make the size of the speckle substantially uniform on the display. The size of speckle in an image produced from transmit ultrasound beams may depend on the frequency of the transmit ultrasound beams.

In particular, generating transmit ultrasound beams at a first frequency throughout one sector and at a second frequency in a second sector may produce images in which the speckle size varies between the first and second sectors. According to the present invention, the frequencies of the transmit ultrasound beams transmitted in a sector of the region alternate. For example, the first sector may be insonified by a first transmit ultrasound beam at a first frequency and a second transmit ultrasound beam transmitted at a second frequency. In one embodiment, the two adjacent transmit ultrasound beams are transmitted at different frequencies.

In addition, the line-by-line frequency interlacing may reduce banding created by the different attenuation characteristics associated with different frequencies by interlacing the transmit ultrasound beams. In particular, ultrasound scan lines generated by higher frequency transmit ultrasound beams may appear dim compared to ultrasound scan lines generated by lower frequency transmit ultrasound beams. According to the present invention, alternating the frequency of transmit ultrasound beams in a sector may produce a display having substantially uniform brightness.

In a further aspect of the present invention, a post summation Time Gain Control (TGC) is used to equalize the different attenuation characteristics of the different frequencies. In particular, a conventional TGC is used to adjust the gain of electrical signals generated from reflected pressure waves created by a first transmit ultrasound beam transmitted at a first frequency. The adjusted electrical signals are then added to form a first receive ultrasound beam.

In a further aspect of the present invention, all of the elements of the ultrasonic transducer are used to generate the transmit ultrasound beams.

According to the present invention, electrical signals generated from reflected pressure waves created by a second transmit ultrasound beam transmitted at a second frequency (which is higher than the first frequency) are added to form a second receive ultrasound beam. The gain of the second receive ultrasound beam is adjusted after the electrical signals are summed. Accordingly, the ultrasound scan lines generated by an ultrasound system using a plurality of frequencies may be displayed at substantially uniform brightness. The cost of the post summation TGC may be less than the cost of constructing a second TGC to adjust the gain of the higher frequency electrical signals. In conventional ultrasound systems the attenuation may be compensated for by adjusting the gain of a particular frequency. If the gain is optimized for the higher frequency ultrasound beam, then the lower frequency electrical signals may create ultrasound scan lines that appear too bright, saturating the display. If the gain is optimized for the lower frequency ultrasound beam, then the higher frequency electrical signals may create ultrasound scan lines that appear too dim.

BRIEF DESCRIPTION OF THE DRAWINGS

FIG. 2 is a flow chart that illustrates operations of an ultrasound imaging system according to the present invention;

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Although the present invention is described herein with reference to One Dimensional (1D) ultrasound transducers producing Two Dimensional images (2D), it will be understood that the scope of the present invention includes Two Dimensional (2D) ultrasound transducer arrays that produce Three Dimensional (3D) or volumetric ultrasound images. In addition, the components of the ultrasound systems described herein may be packaged as a single unit or packaged separately and interconnected to provide the functions described herein. The ultrasound pressure waves described herein propagate through tissue in a region of a body. The term "tissue" includes blood and organs such as those found in a human body, such as a heart. Like numbers refer to like elements throughout.

Spatial Separation of Transmit Ultrasound Beams

Figure 1A:
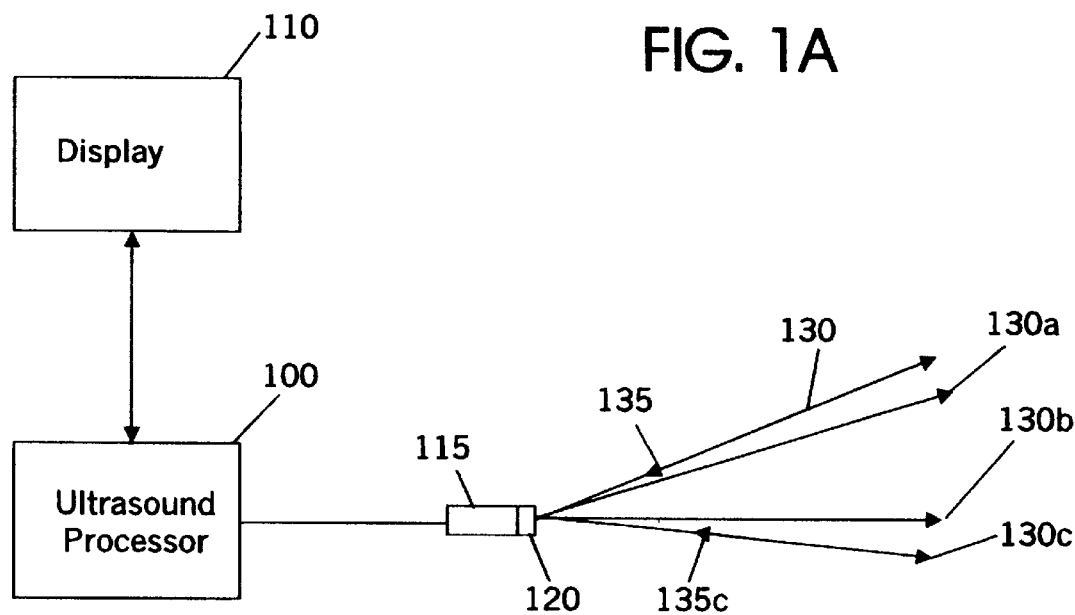
FIG. 1A is a block diagram of an ultrasound imaging system according to the present invention.

FIG. 1A is a block diagram of an ultrasound imaging system according to an embodiment of the present invention. In particular, an ultrasound processor 100 provides excitation, such as electrical signals, to an ultrasound transducer 120 (which may be mounted in an ultrasound probe) that converts the excitation to corresponding ultrasound pressure waves. The ultrasound transducer 120 comprises a plurality of ultrasound transducer elements arranged in an array or in a linear fashion and electrically connected to the ultrasound processor 100. For example, the ultrasound transducer 120 may comprise 256 ultrasound transducer elements arranged in an array of 16×16 ultrasound transducers elements that may be independently excited by the ultrasound processor 100. The array may be arranged to approximate an ultrasound transducer having a circular aperture. The ultrasound transducer 120 converts electrical signals from the ultrasound processor 100 into pressure waves that propagate through the region 140. The ultrasound transducer 120 also converts reflected pressure waves from region 140 to electrical signals that are provided to the ultrasound processor 100. The ultrasound processor 100 processes the electrical signals from the ultrasound transducer 120 to provide ultrasound scan lines for display on display 110.

The ultrasound processor 100 generates electrical signals which produce a plurality of transmit ultrasound beams 130, 130a, 130b, 130c from the ultrasound transducer 120, to insonify the region 140. The ultrasound processor 100 may comprise a volumetric ultrasound machine, a volumetric processor upgrade to a conventional 2D ultrasound machine, a 2D ultrasound machine which is programmed to perform the operations described herein, a general purpose computer, or combinations thereof.

As the transmit ultrasound beam 130 propagates through the region 140, a portion of the pressure wave may be reflected back towards the ultrasound transducer 120. For example, when the transmit ultrasound beam 130 encounters tissue having different acoustical impedance, a reflected pressure wave 135 is generated which propagates through the region 140 back towards the ultrasound transducer 120. As the pressure wave 135 encounters more tissue having different acoustical properties, respective reflected pressure waves are created. Accordingly, a plurality of reflected pressure waves are created by the transmit ultrasound beam 130 propagating through the region 140. Although not shown, it will be understood that each of the transmit ultrasound beams 130, 130a, 130b, 130c create respective pressure waves that are analogous to the reflected pressure wave 135.

The ultrasound transducer 120 converts the plurality of reflected pressure waves to electrical signals which are processed by the ultrasound processor 100 to generate a corresponding receive ultrasound beam. The corresponding receive ultrasound beam is displayed as an ultrasound scan line on a display 110. The display 110 may comprise a Cathode Ray Tube (CRT), Liquid Crystal Display (LCD) or other display known to those having skill in the art.

Figure 1B:
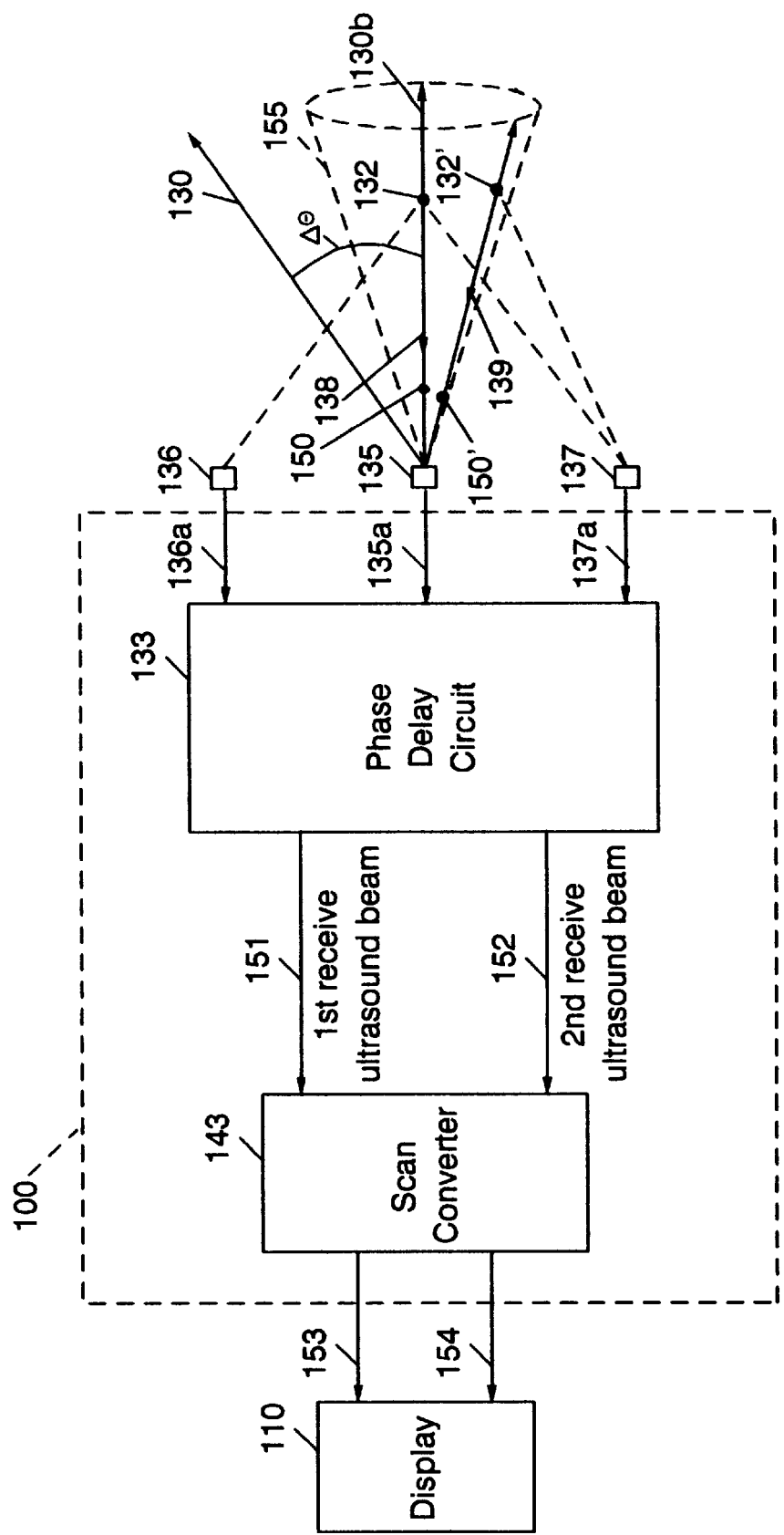
FIG. 1B is a block diagram of an embodiment of an ultrasound image system according to the present invention.

FIG. 1B is a block diagram that illustrates the generation of a plurality of receive ultrasound beams according to an embodiment of the present invention. As shown in FIG. 1B, includes a phase delay circuit 133 which focuses on the propagation paths of transmit ultrasound beams generated by the ultrasound processor to provide respective receive ultrasound beams. The phase delay circuit 133 focuses on a point on the path of propagation of the transmit ultrasound beam 130b by adjusting the phase delay of electrical signals that correspond to the reflected pressure wave created at that point received by an ultrasound transducer element. For example, the phase delay circuit 133 focuses on a point 132 on the path of propagation of the transmit ultrasound beam 130b by time aligning electrical signals 136a, 137a created by the pressure wave reflected from the point 132 to the ultrasound transducer elements 136, 137.

The electrical signals 136a, 137a are time aligned (beamformed) by delaying the phase of the electrical signals 136a, 137a using a phase delay circuit 133. The phase delay for each electrical signal 136a, 137a is based on the distance from the point 132 to the respective ultrasound transducer element 136, 137 that generates the electrical signals 136*a*, 137*a*. Therefore, the electrical signals are aligned in time by the phase delay and are added together. For example, if the first ultrasound transducer element 137 receives a reflected pressure wave from the point 132 and the second ultrasound transducer element 136 also receives the reflected pressure wave from the point 132, the electrical signals 136*a*, 137*a* are time aligned by the phase delay circuit by adjusting their respective phases based on the distance from the point 132 to the respective ultrasound transducer element 136, 137. It will be understood that the electrical signals 136*a*, 137*a* may be beamformed using other techniques known to those of skill in the art.

The phase delay circuit 133 focuses on a plurality of points on the transmit ultrasound beam 130*b* dynamically to form a first receive ultrasound beam 151. In particular, a plurality of reflected pressure waves are generated at a respective plurality of points at different distances on the path of propagation of the transmit ultrasound beam 130*b*. Accordingly, the phase delay circuit 133 uses different phase delay adjustments to focus on each of the plurality of points on the path of propagation. In other words, as the phase delay circuit 133 focuses on points on the path of propagation, the phase delays are updated to focus on points that are located at different distances on the path. For example, the phase delay circuit 133 uses different phase delay adjustments to focus on points 150, 150' than on the points 132, 132'.

The phase delay circuit 133 also generates a plurality of receive ultrasound beams from a single transmit ultrasound beam using parallel receive processing. In general, the transmit ultrasound beam is broadened, as described herein, to insonify the region 140. The phase delay circuit 133 generates the plurality of receive ultrasound beams by dynamically focusing on a plurality of propagation paths that lie inside an envelope 155 of the broadened transmit ultrasound beam.

According to FIG. 1B, the first receive ultrasound beam 151 is formed by dynamically focusing on a propagation path that corresponds to a first reflected pressure wave 138 as described above. A second receive ultrasound beam 152, which corresponds to a second reflected pressure wave 139, is formed using parallel receive processing. First and second points 132, 132' are located equidistant from an ultrasound transducer element 135 in the region 140. However, because the first and second points 132, 132' are located on the different propagation paths, the respective distances from the first and second points 132, 132' to the ultrasound transducer element 137, may be different. Consequently, the phase delay circuit 133 adjusts the phase of the electrical signals 136*a*, 137*a* corresponding to the first and second reflected pressure waves 138, 139 by different amounts. For example, the first reflected pressure wave 138 corresponds to a first receive ultrasound beam 151 and the second reflected pressure wave 139 corresponds to a second receive ultrasound beam 152.

The first receive ultrasound beam 151 is formed by adjusting the phase delay of the electrical signals that correspond to the first reflected pressure wave 138 based on the difference in the distances from the first point 132 to each of the ultrasound transducer elements that generate electrical signals that correspond to the first reflected pressure wave 138. The second receive ultrasound beam 152 is formed by adjusting the phase delay of the electrical signals that correspond to the second reflected pressure wave 138 based on the difference in the distances from the second point 132' to each of the ultrasound transducer elements that generate electrical signals that correspond to the second reflected pressure wave 139. Consequently, the phase delay circuit 133 may use different phase delay adjustments for the electrical signals that correspond to the first and second receive ultrasound beams 151, 152. As described herein, the term tracking includes dynamic focusing and parallel receive processing. For example, tracking refers to the formation of receive ultrasound beams using dynamic focusing or parallel receive processing.

A scan converter 143 converts the first and second receive ultrasound beams 151, 152 to first and second ultrasound scan lines 153, 154 by converting the coordinates used to represent the region 140 to coordinates used to address the display. For example, the region 140 may be represented in polar coordinates and the display 110 may be addressed with cartesian coordinates. Therefore, the scan converter 143 may convert polar coordinates to Cartesian coordinates to display the first and second ultrasound scan lines 153, 154.

FIG. 2 is a flowchart that illustrates operations of an ultrasound system utilizing spatially separated transmit ultrasound beams according to the present invention. Processing begins in block 145. The ultrasound processor 100 generates a first transmit ultrasound beam in a first direction by exciting the transducer 120 with an excitation (block 150).

After a settling time (block 152), the ultrasound processor 100 generates a second transmit ultrasound beam in a second direction by providing a second excitation to the ultrasound transducer 120 (block 155). The ultrasound processor 100 then tracks the first and second transmit ultrasound beams as they propagate through the region 140 (block 160).

If the desired portion of the region 140 has not been scanned (block 165), the ultrasound processor 100 generates a third direction by incrementing the first direction (block 170) and repeats the generation of transmit ultrasound beams as described in blocks 150–160 using new directions until the desired portion of the region 140 has been scanned (block 165). When the desired portion of the region 140 has been scanned (block 165), processing ends.

Figure 3A:
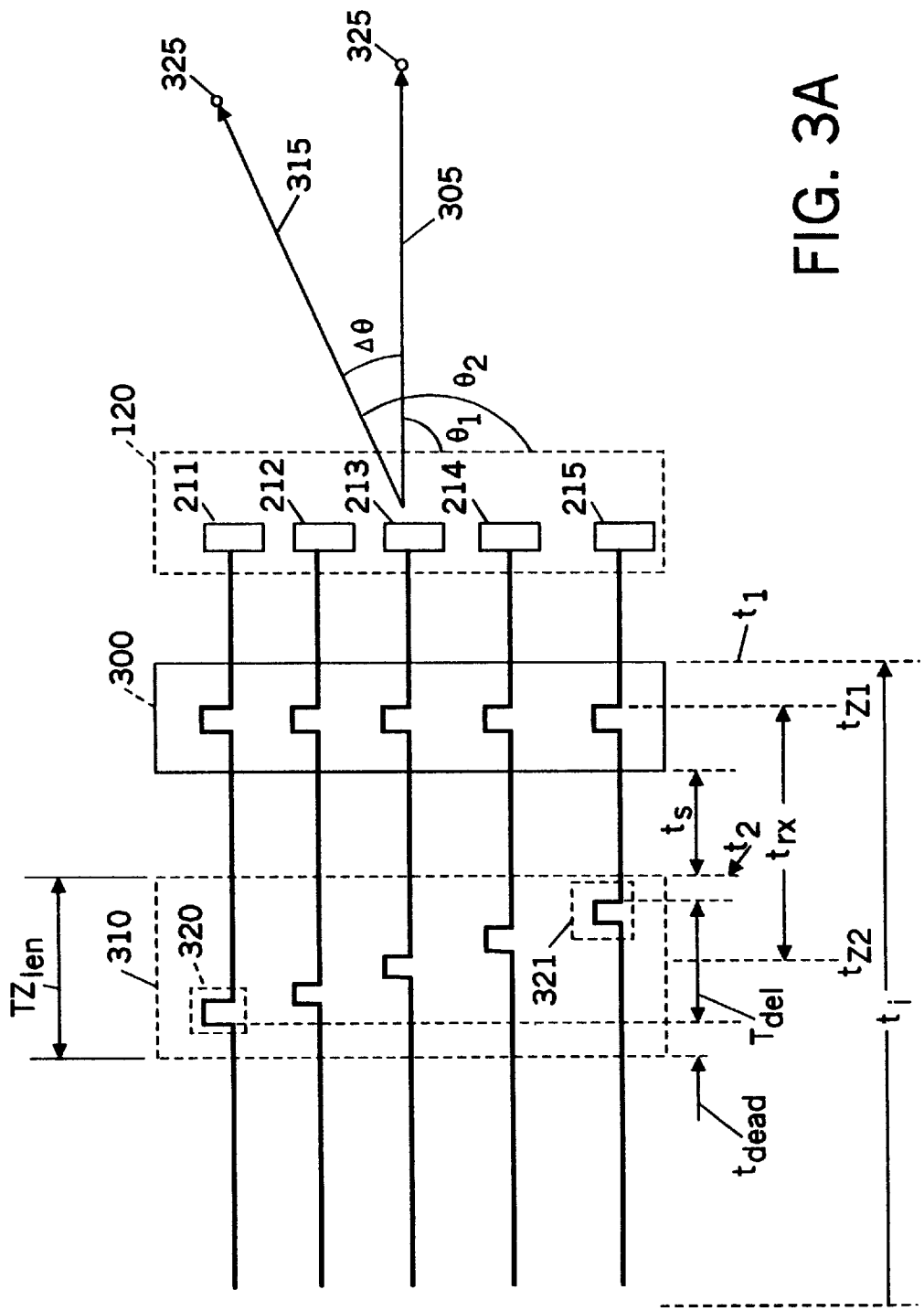
FIG. 3A is a diagram of spatially separated transmit ultrasound beams and associated signals according to the present invention.

FIG. 3A is a diagram of spatially separated transmit ultrasound beams according to the present invention. The ultrasound transducer elements 211–215 are excited with a first excitation in a first transmit zone 300 which causes the ultrasound transducer 120 to generate a first transmit ultrasound beam 305 focused at a maximum scan range 325 at an angle $\theta_1$ with respect to the face of the ultrasound transducer 120.

The ultrasound transducer elements 211–215 are then excited by a second excitation in a second transmit zone 310 after a settling time interval $t_s$ following the first excitation by about 0.5–10 $\mu$s in a maximum scan range interval $t_s$. The settling time interval is determined such that the ultrasound transducer elements 211–215 settle (or ring down) from the first excitation before beginning the second excitation. The second excitation generates a second transmit ultrasound beam 315 focused at the maximum scan range 325 at angle $\theta_2$ with respect to the surface of the ultrasound transducer 120. The two transmit ultrasound beams 305, 315 separated by the angle $(\theta_2-\theta_1)$ propagate from the ultrasound transducer 120 through the region 140. As the first and second transmit ultrasound beams 305, 315 propagate, parallel receive processing tracks each transmit ultrasound beam.

The first transmit ultrasound beam 305 is generated in a first direction at the first start time $t_1$ and the second transmit ultrasound beam 315 is generated in a second direction at the second start time $t_2$ according to the excitations described above. The signals included in the first excitation are phased to generate the first transmit ultrasound beam 305 in the first direction. The signals included in the second excitation are phased to generate the second transmit ultrasound beam 315 in the second direction. The respective directions of the first and second transmit ultrasound beams 305, 315 define a separation angle Δθ therebetween. It will be understood that the scope of the present invention includes the generation of more than two transmit ultrasound beams during the maximum scan range interval. For example, the present invention may be practiced by generating four transmit ultrasound beams, wherein each of the transmit ultrasound beams is generated at about the same frequency. For example, in an ultrasound system that transmits four transmit ultrasound beams, all four transmit ultrasound beams may be generated at 2.5 MHz. However, it will be understood by those skilled in the art that other frequencies may be used.

The first and second excitations 300, 310 fall within respective first and second transmits zones 300, 310 which are separated by the settling time interval $t_s$. The settling time interval is the time from the end of the first transmit zone 300 to the beginning of the second transmit zone 300. The settling time interval allows the ultrasound transducer elements 112, 115 in the ultrasound transducer 120 to stop oscillating before the second excitation begins. The present invention may thereby maintain a consistent energy density for the transmit ultrasound beams compared to a conventional scanner. The present invention may thereby preserve image quality while increasing the data acquisition (frame) rate.

The total time duration of the first and second transmit zones 300, 310, as shown for zone 310, comprises two times: the excitation signal duration and the delay profile time. The duration of an excitation signal $P_{len}$, is given by:

$$P_{len} = \frac{N}{f_0} \quad (1)$$

where $f_0$ is the frequency of the excitation signal in MHz and N is the number of cycles in the excitation signal. The delay profile time, $T_{del}$, is the time difference between the first excitation signal 321 and the last excitation signal 320 applied to the ultrasound transducer 120. As described above, the delay may be used to focus or steer the transmit ultrasound beam in the region 140. For a circular aperture, the delay profile time $T_{del}$, is given by:

$$T_{del} (\mu s) \approx \frac{d(\sin \theta)}{c} \quad (2)$$

where d is the diameter of the transmit aperture, and c is the speed of sound in the region 140 (1.54 mm/μs for tissue), and θ is angle at which the transmit ultrasound beam is steered.

The total time duration of a transmit zone 300, 310 is given by:

$$TZ_{len} = T_{del} + P_{len} + t_{dead} \quad (3)$$

where $t_{dead}$ is an electronic reset time between transmit zones. In a preferred system $t_{dead}$ is about 200 ns.

An ultrasound system using spatial separation of transmit ultrasound beams, according to the present invention, may use a 2 cycle pulse as the excitation signal 320. A scan using a Δθ of about 40° at 2.5 MHz with 2 cycles may therefore use a total time duration for a transmit zone ($TZ_{len}$) of 3.8 μs. Four transmit zones may, therefore, produce a total transmit time of about 15.2 μs.

Figure 3B:
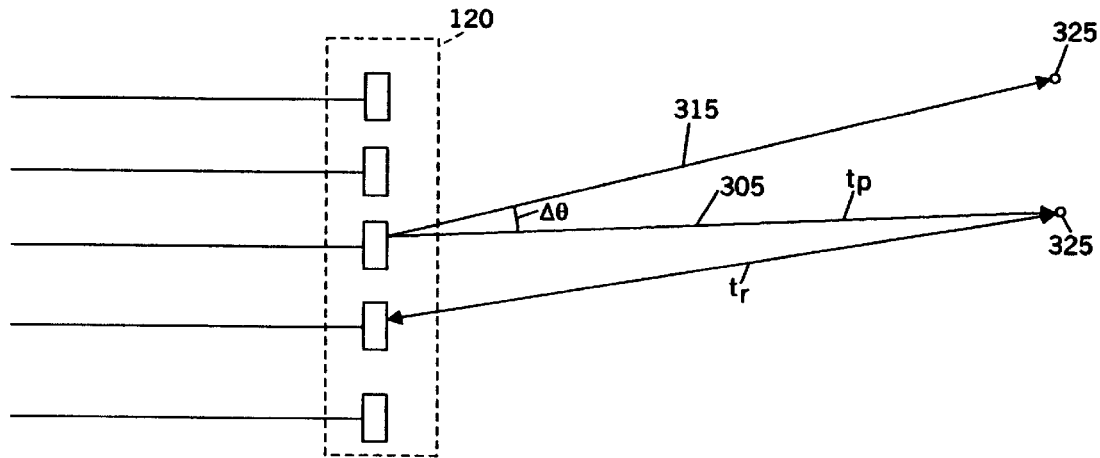
FIG. 3B is a diagram that illustrates the maximum scan range interval associated with the maximum scan range.

FIG. 3B is a diagram that illustrates the maximum scan range interval associated with the maximum scan range 325. As shown in FIG. 3B, the first transmit ultrasound beam 305 generated at the first start time $t_1$ propagates to the maximum scan range 325 in a propagation time $t_p$. A reflected pressure wave is created by the first transmit ultrasound beam 305 at the maximum scan range 325 which propagates back to the ultrasound transducer 120 in a reflection time $t_r$. The sum of the propagation time and the reflection time represents the maximum scan range interval which is greater than a time interval from the first start time to the second start time. The plurality of transmit ultrasound beams are generated before the reflected pressure wave created by the first transmit ultrasound beam 305 reaches the ultrasound transducers (i.e., within the maximum scan range interval).

The maximum scan range interval time, $t_i$, may be defined in relation to the time needed to acquire a single ultrasound scan line. In particular, the time needed to acquire an ultrasound scan line may be limited by the speed of sound in the region 140. The time to acquire one ultrasound scan line can be expressed as:

$$t_i = 2R/c \quad (4)$$

where R is the maximum scan range of the ultrasound scan and c is the speed of sound in the medium. Therefore, for a scan depth of 15 cm and a speed of sound of 1.54 mm/μs, the maximum scan range time interval is about 200 μs. Accordingly, the plurality of transmit ultrasound beams may be generated in less than 200 μs.

It will be understood that the first transmit ultrasound beam 305 continues to propagate through the region 140 beyond the maximum scan range 325. Reflections created beyond the maximum scan range 325 are received at the ultrasound transducer 120 after the maximum scan range interval and are, therefore, ignored. According to the present invention, the second transmit ultrasound beam 315 is generated before the maximum scan range interval elapses. Consequently, the present invention allows an increase in the number of transmit ultrasound beams used to insonify the region 140 within a given time period, thereby increasing the data acquisition rate.

Because the second transmit ultrasound beam 315 is generated before all of the reflections created by the first transmit ultrasound beam 305 have been received by the ultrasound transducer 120, there may be interference between the first transmit ultrasound beam 305 and the second transmit ultrasound beam 315. The angle of separation Δθ is preferably chosen according to the present invention to minimize such interference.

The interference is caused by the diffraction of the transmit ultrasound beams in the region. In particular, energy diffracted from a first transmit ultrasound beam (steered in a first direction) may overlap a second transmit ultrasound beam (steered in a second direction). The overlap may cause a receive ultrasound beam, formed by tracking the second transmit ultrasound beam to include interference from the first transmit ultrasound beam. Moreover, inaccuracy in the tracking of the second transmit ultrasound beam may cause additional diffracted energy from the first transmit ultrasound beam to be included in the receive ultrasound beam, thereby increasing the interference between the first and second transmit ultrasound beams. Separating the transmit ultrasound beams by a separation angle, however, may reduce the interference described above.

In a preferred embodiment using more than two transmit ultrasound beams according to the present invention, the separation angle is in a range between about 10 to 30 degrees to reduce the interference. In a preferred embodiment using two transmit ultrasound beams according to the present invention, the separation angle should be in a range between about 10 to 20°.

Referring again to FIG. 3A, as the first and second transmit ultrasound beams 305, 315 propagate through the region 140, the corresponding reflected pressure waves are received by the ultrasound transducer 120. A first zero time $t_{z1}$ is established before which no reflected pressure waves are processed by the ultrasound processor 100. For example, a first zero time $t_{z1}$ may be established at the center of the first transmit zone which corresponds to a distance. The first zero time $t_{z1}$ is equal to the time needed for the first transmit ultrasound beam to propagate to the distance plus the time needed for corresponding reflected pressure wave to propagate back to the ultrasound transducer 120 from the distance.

The ultrasound processor 100 begins processing reflected pressure waves from the second transmit ultrasound beam 315 at a second zero time $t_{z2}$. The second zero time $t_{z2}$ is delayed from the first zero time $t_{z1}$ by the receive offset $t_{rx}$. The receive offset is defined by the time difference between the center of the first and second transmit zones 300, 310. The second zero time is the first zero time plus the receive offset. The zero times are centered in the respective transmits zones to enable consistant beamforming despite the different angles used to steer the transmit ultrasound beams.

Where more than two transmit ultrasound beams are generated during the maximum scan range interval, a zero time is determined for each transmit ultrasound beam generated. The zero time is determined by adding a corresponding receive offset to the first zero time, $t_{z1}$. The corresponding receive offset is the difference between the center time of the first transmit zone 300 and the center time of the transmit zone which generated the particular transmit ultrasound beam for which the receive offset is desired.

Figure 4:
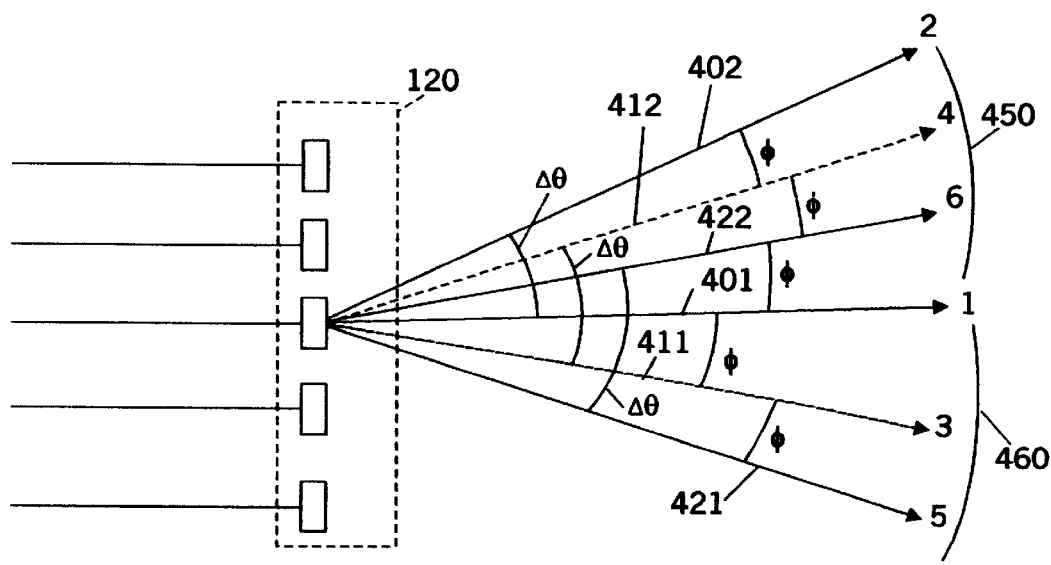
FIG. 4 is a diagram that illustrates a plurality of transmit ultrasound beams used to insonify the region according to an embodiment of the present invention.

FIG. 4 is a diagram that illustrates a plurality of transmit ultrasound beams used to insonify the region 140 according to the present invention. A first transmit ultrasound beam 401 is generated in a first direction and a second transmit ultrasound beam 402 is generated in a second direction, thereby defining the separation angle Δθ therebetween. After a first maximum scan range interval elapses, a third transmit ultrasound beam 411 is generated in a third direction and a fourth transmit ultrasound beam 412 is generated in a fourth direction, thereby defining the separation angle Δθ therebetween. After a second maximum scan range interval elapses, a fifth transmit ultrasound beam 421 is generated in a fifth direction and a sixth transmit ultrasound beam 422 is generated in sixth direction, thereby defining the separation angle Δθ therebetween. Consequently, the data acquisition rate may be increased by a factor of two as compared to a conventional system wherein only one transmit ultrasound beam is generated in each maximum scan range interval time.

As shown in FIG. 4, the first, third, and fifth transmit ultrasound beams 401, 411, 421 are generated adjacent to each other to insonify a sector 460 of the region 140. The second, fourth, and sixth transmit ultrasound beams 402, 412, 422 are generated adjacent to each other to insonify a sector 450 of the region 140. The first, third, and fifth transmit ultrasound beams 401, 411, 421, are separated by an incremental angle φ. The second, fourth, and sixth transmit ultrasound beams 402, 412, 422 are separated by the incremental angle φ. The respective directions for each of the adjacent transmit ultrasound beams in sector 460 is defined by adding the incremental angle φ to the previously generated adjacent transmit ultrasound beam. For example, the third direction (of 411) is defined by changing the first direction (of 401) by the incremental angle φ.

Figure 5:
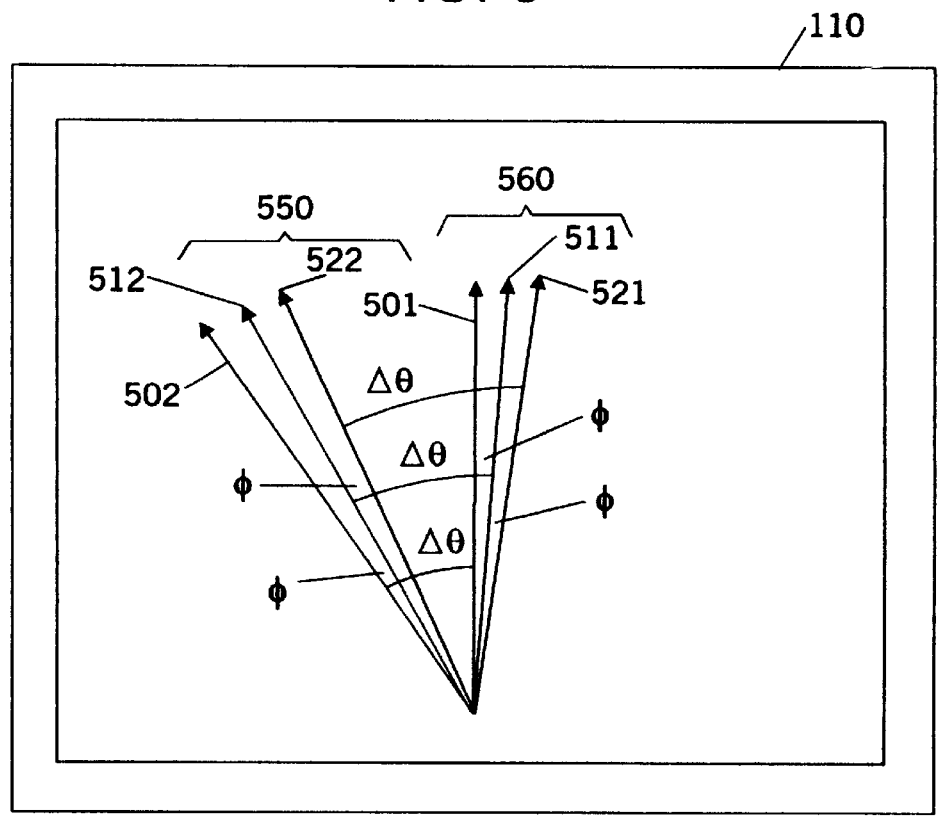
FIG. 5 is a diagram that illustrates a display of ultrasound scan lines according to an embodiment of the present invention.

FIG. 5 is a diagram illustrating a display of ultrasound scan lines according to the present invention. The reflected pressure waves generated by the transmit ultrasound beams in FIG. 4 are processed by the ultrasound processor 100 to provide respective ultrasound scan lines to the display 110. The ultrasound scan lines are displayed according to the order in which the respective transmit ultrasound beams are generated. In particular, the first and second ultrasound scan lines 501, 502 are displayed having the separation angle Δθ therebetween and correspond to the first and second transmit ultrasound beams 401, 402. The third and fourth ultrasound scan lines 511, 512 are displayed having the separation angle Δθ therebetween and correspond to the third and fourth transmit ultrasound beams 411, 412. The fifth and sixth ultrasound scan lines 521, 522 are displayed having the separation angle θ therebetween and correspond to the fifth and sixth transmit ultrasound beams 421, 422. The display of the first, third and fifth transmit ultrasound scan lines 501, 511, 521 defines a first display sector 560. The display of the second, fourth, and sixth ultrasound scan lines 502, 512, 522 defines a second display sector 550.

Spectral and Spatial Separation of Transmit Ultrasound Beams

Interference between transmit ultrasound beams generated during the maximum scan range interval may be further reduced by spectrally separating the transmit ultrasound beams.

Figure 6A:
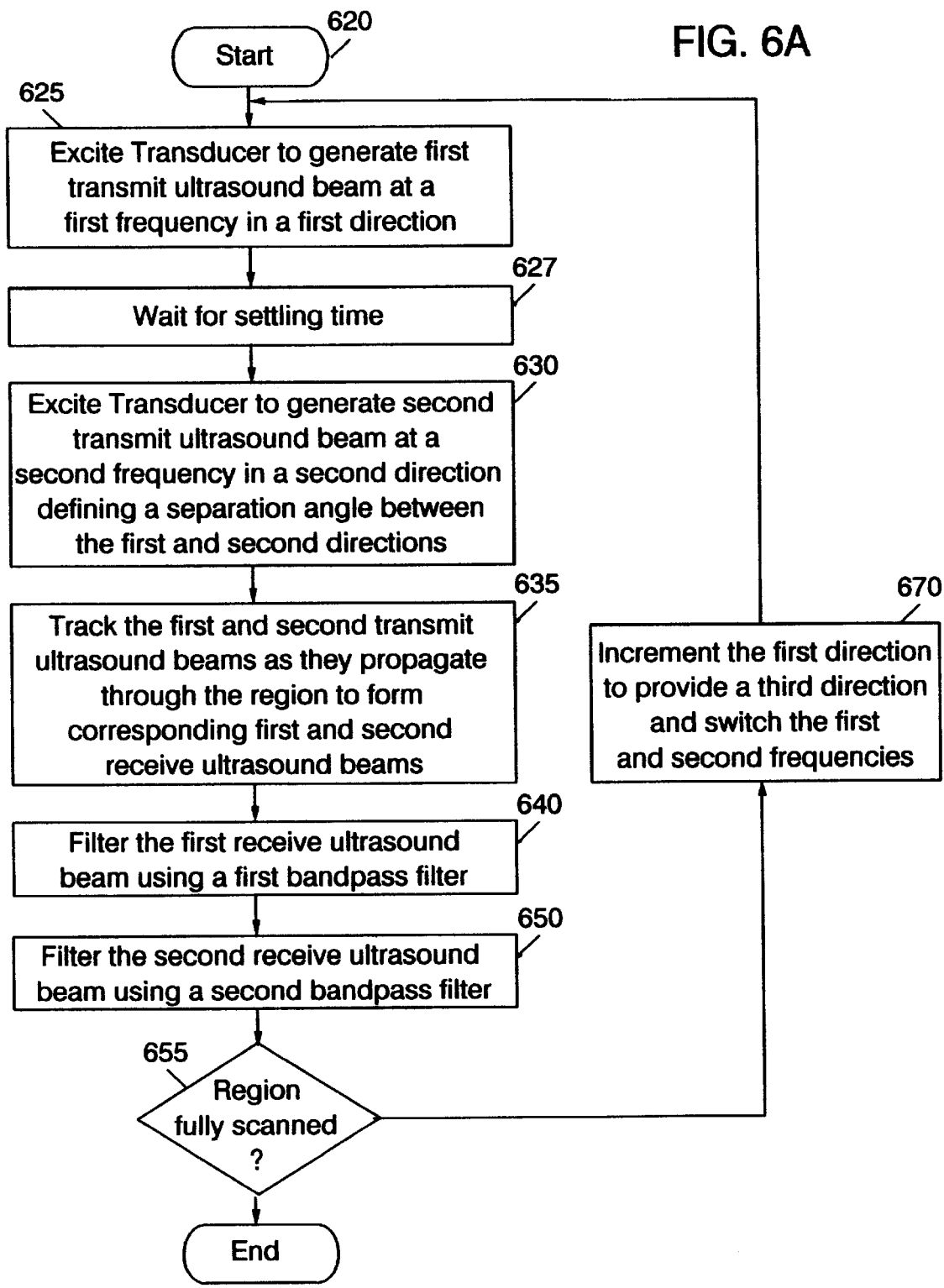
FIG. 6A is a flowchart that illustrates operations of an ultrasound system using spectral and spatial separation of transmit ultrasound beams according to an embodiment of the present invention.

FIG. 6A is a flowchart that illustrates operations of an ultrasound system utilizing spatially and spectrally separated transmit ultrasound beams according to an embodiment of the present invention. Processing starts in block 620. The ultrasound processor 100 generates a first ultrasound beam at a first frequency in a first direction by exciting the transducer 120 (block 625). After a settling time, which is less than the maximum scan range interval time (block 627), the ultrasound processor 100 generates a second ultrasound beam at a second frequency in a second direction, the first and second directions having a separation angle Δθ therebetween (block 630).

The ultrasound processor 100 then tracks the first and second transmit ultrasound beams as they propagate through the region 140 (block 635) to form first and second receive ultrasound beams. The first receive ultrasound beams is filtered using a first bandpass filter (block 640). The second receive ultrasound beam is filtered using a second bandpass filter (block 650). If the region 140 has not yet been fully scanned (block 655), the ultrasound processor 100 increments the first direction to provide a third direction to be used as the first direction in block 625 and switches the first and second frequencies (block 670). For example, in a second iteration of the flowchart in FIG. 6A the first transmit ultrasound beam is generated at a frequency which is different than in the first iteration. When the desired portion of the region 140 has been scanned (block 655), processing ends.

Figure 6B:
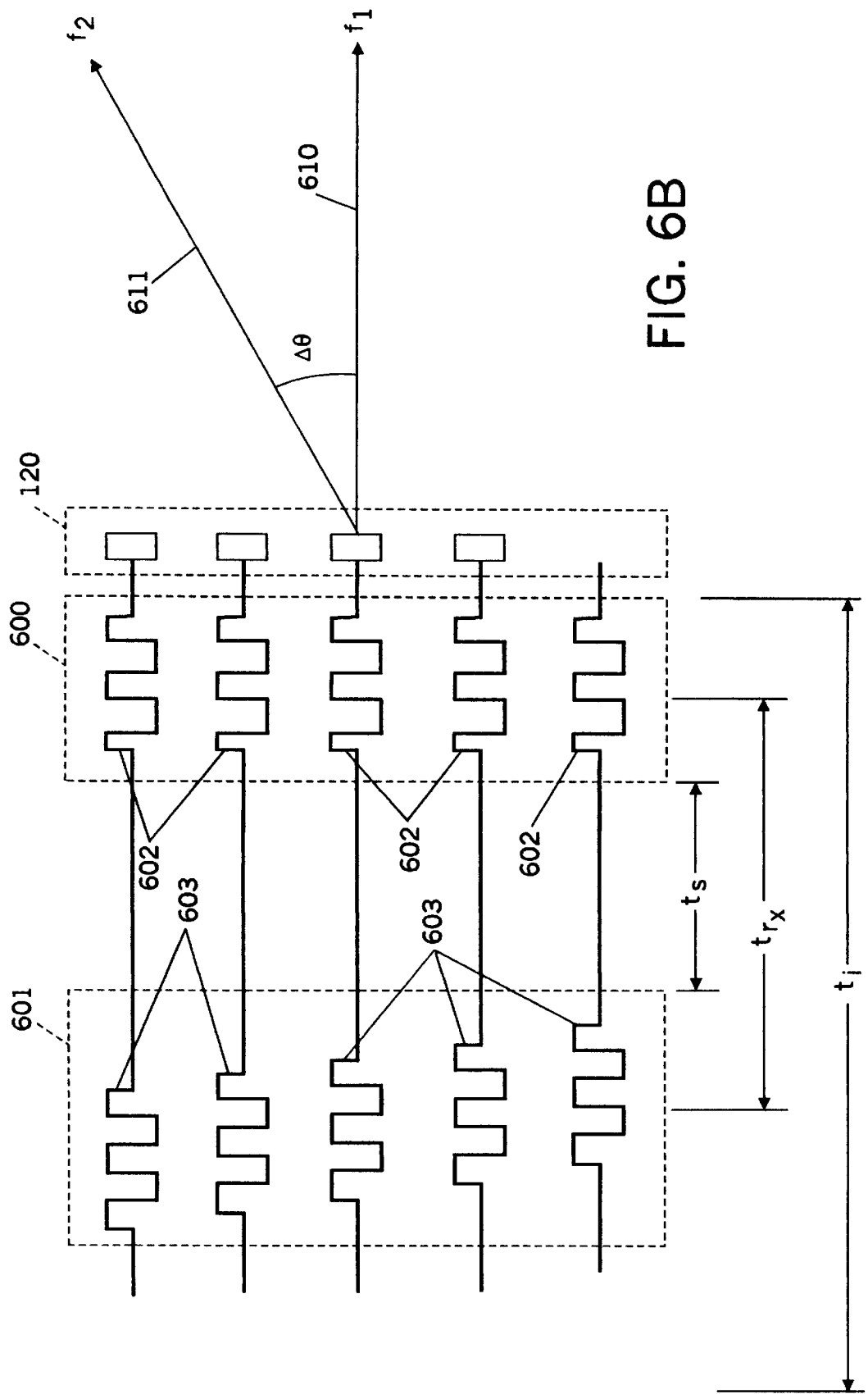
FIG. 6B is a diagram that illustrates spectrally and spatially separated transmit ultrasound beam and associated signals according to an embodiment of the present invention.

As shown in FIG. 6B, a first excitation in a first transmit zone 600 generates a first transmit ultrasound beam 610 at a first frequency, $f_1$, in a first direction and a second excitation in a second transmit zone 601 generates a second transmit ultrasound beam 611 at a second frequency, $f_2$, in a second direction. According to one aspect of the present invention, using different frequencies for the first and second transmit ultrasound beams 610, 611 provides a basis upon which the corresponding reflected pressure waves may be tracked by the ultrasound processor 100. The spatially and spectrally separated transmit ultrasound beams 610, 611 may thereby provide an increased data acquisition rate compared to conventional systems while further reducing interference between transmit ultrasound beams.

The first excitation includes a first plurality of signals 602 each having an associated first frequency $f_1$ for the signals and the second excitation includes a second plurality of signals 603 each having an associated second frequency $f_2$ for the signals. The first plurality of signals are offset (phased) to generate the first transmit ultrasound beam 610 in the first direction. The second plurality of signals are offset (phased) to generate the second transmit ultrasound beam 611 in the second direction. The respective directions of the first and second transmit ultrasound beams 610, 611 define the separation angle $\Delta\theta$ therebetween. Although the present invention is described in reference to the generation of two transmit ultrasound beams having different frequencies, it will be understood that more than two transmit ultrasound beams at a corresponding number of frequencies may be generated during the maximum scan range interval. For example, six transmit ultrasound beams may be generated at six different frequencies.

The first and second excitations are included in respective first and second transmits zones 600, 601 which are separated by the settling time interval $t_s$. The settling time interval is the time from the end of the first transmit zone 600 to the beginning of the second transmit zone 601. The settling time interval allows the ultrasound transducer elements in the ultrasound transducer 120 to stop oscillating before the second excitation begins. The present invention may therefore maintain a consistent energy density for each transmit ultrasound beam as contrasted with conventional systems having only one excitation per maximum scan range interval time, which may provide an improvement in the quality of the image while increasing the data acquisition rate.

The total time duration of the respective transmit zones can be determined by reference to the equations (1) to (4) related to the total time duration of transmit zones associated with spatially separated transmit ultrasound beams. In addition, parallel receive processing may be used in conjunction with the spatially and spectrally separated transmit ultrasound beams described herein.

Figure 7A:
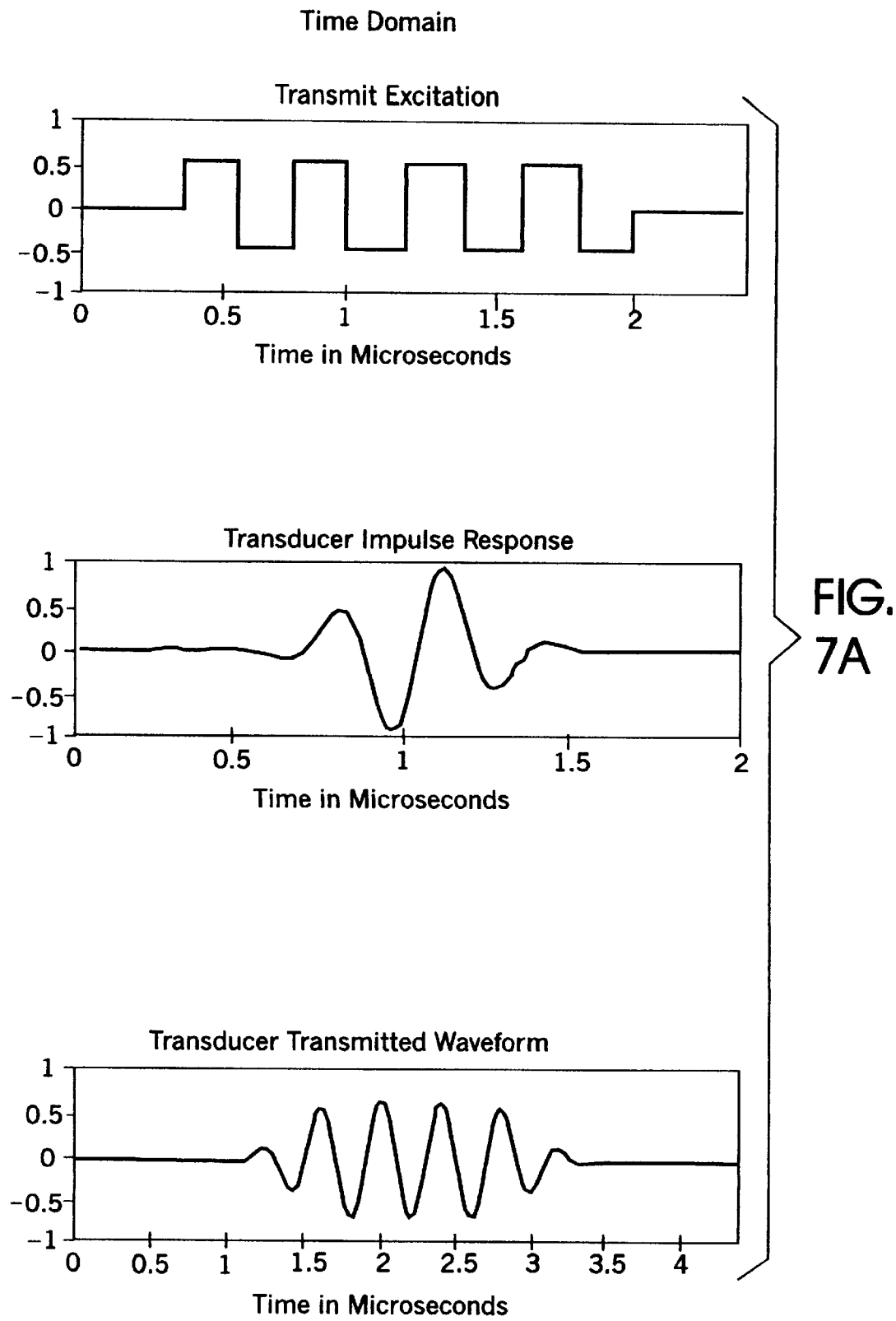
FIG. 7A is a series of graphs that illustrate an exemplary excitation signal used to generate a 2.5 MHz transmit ultrasound beam according to an embodiment of the present invention.

FIG. 7A is a series of graphs that illustrate an exemplary excitation signal used to generate a 2.5 MHz transmit ultrasound beam according to the present invention. The top graph illustrates a 400 ns period square wave excitation signal with a duty cycle of 50%. The middle graph is the impulse response of a Gaussian shaped, 3.0 MHz center frequency, 66% Bandwidth ultrasound transducer. The bottom graph is the pulse transmitted from the ultrasound transducer 120 in response to the excitation signal.

Figure 7B:
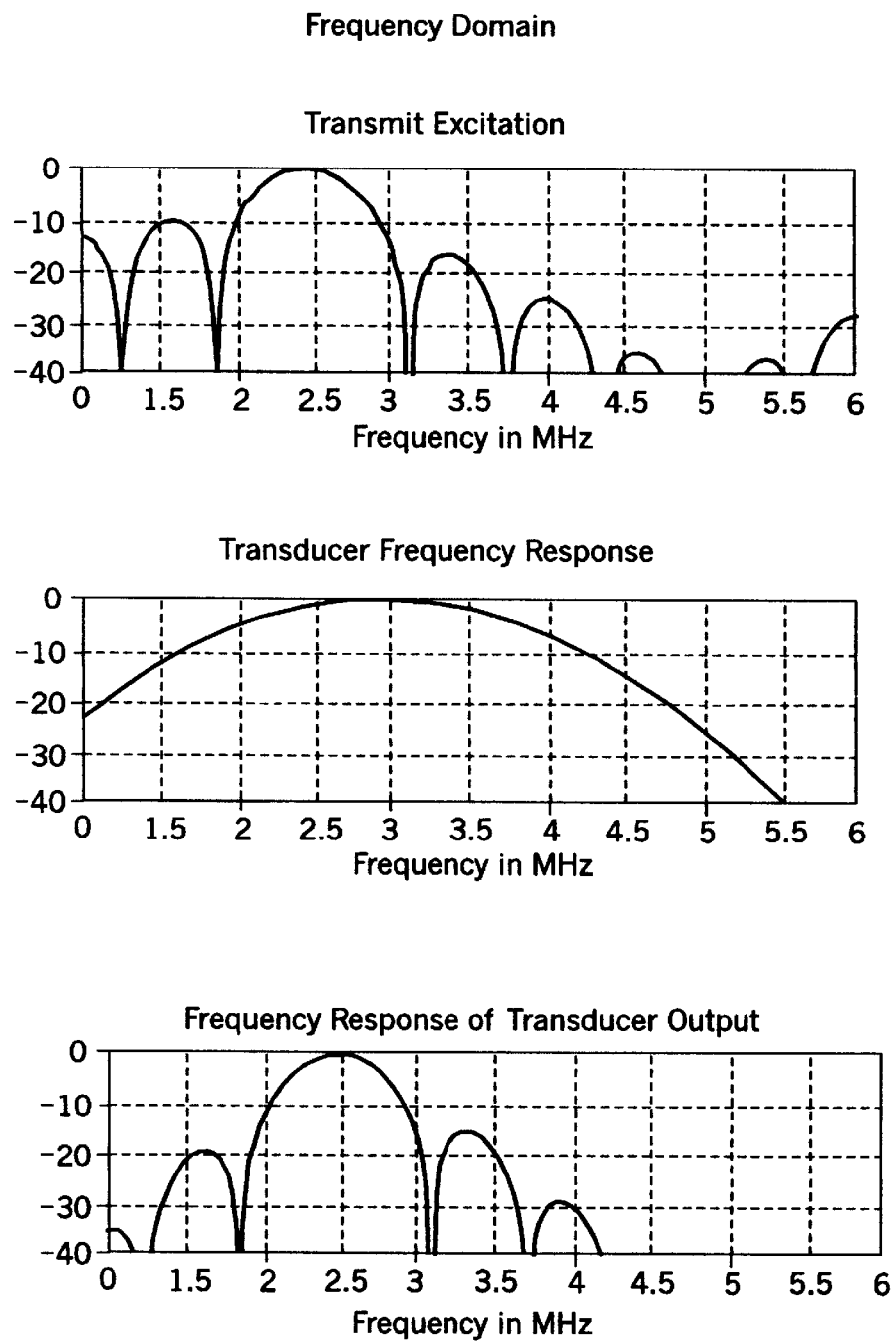
FIG. 7B is a series of graphs that illustrate the exemplary graphs of FIG. 7A in the frequency domain.

FIG. 7B is a series of graphs that illustrate the exemplary graphs of FIG. 7A in the frequency domain. The top graph illustrates the frequency content of the 400 ns period, 50% duty cycle square wave. The middle graph is the frequency response of the ultrasound transducer 120. The bottom graph is the frequency content of the transmit ultrasound beam generated in response to the excitation of the ultrasound transducer with the 400 ns, 50% duty cycle square wave. The ultrasound transducer 120 transmit pulse frequency content shows that the 2.5 MHz transmit pulse may contain energy in the range between about 3.25 to 3.75 MHz which is about 16 dB less than that found at 2.5 MHz. Consequently, a receive filter which is meant to only pass the second transmit at 3.5 MHz may decrease the peak interference from the first 2.5 MHz transmit by about 16 dB.

Figure 8A:
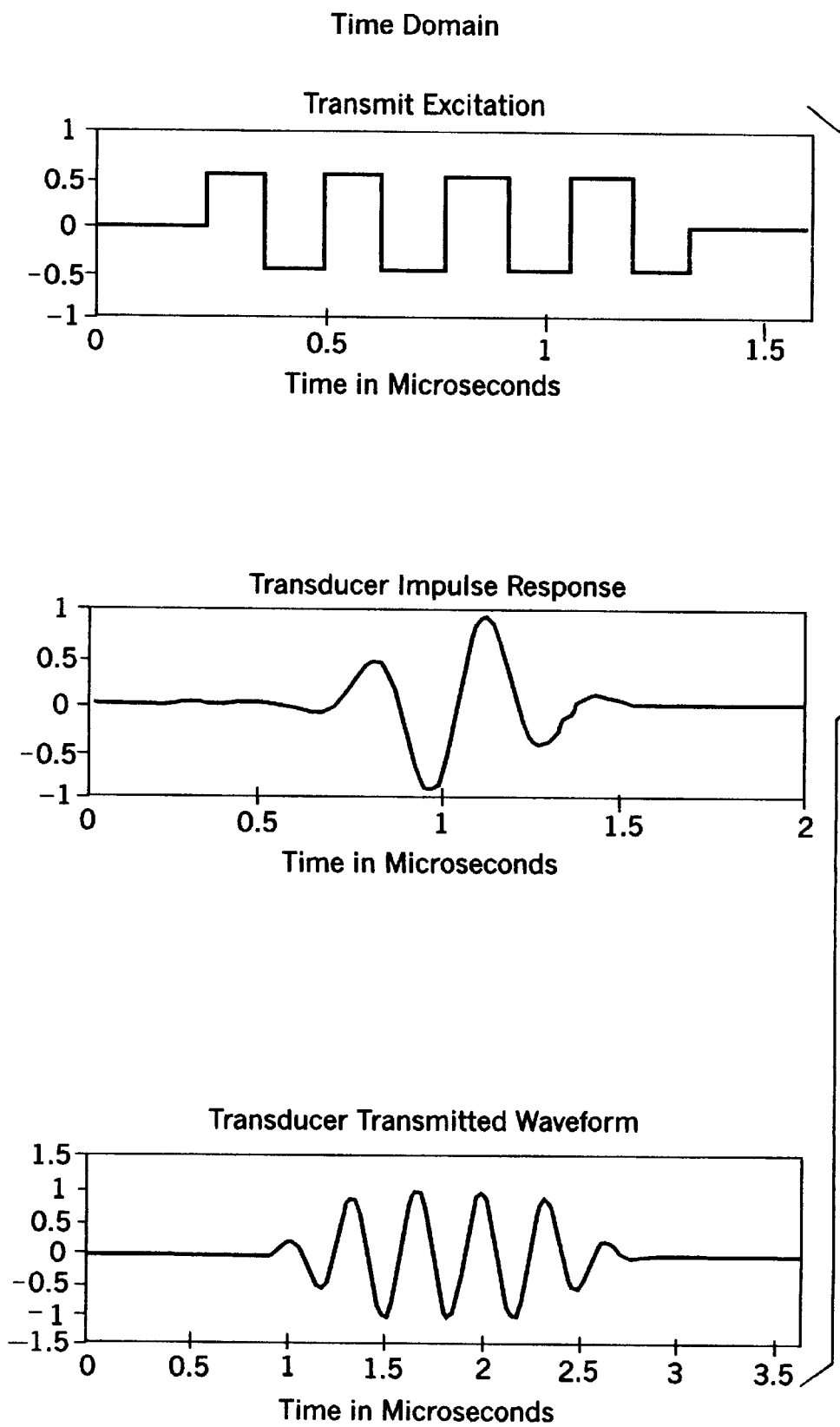
FIG. 8A is a series of graphs that illustrate an exemplary excitation signal used to generate a 3.5 MHz transmit ultrasound beam according to an embodiment of the present invention.

FIG. 8A is a series of graphs that illustrate an exemplary excitation signal used to generate a 3.5 MHz transmit ultrasound beam according to the present invention. The top graph illustrates a four cycle, 286 ns period square wave excitation signal with a duty cycle of 50%. The middle graph is the impulse response of the ultrasound transducer 120 using a Gaussian shaped, 3.0 MHz center frequency, 66%—6 dB Bandwidth ultrasound transducer. The bottom graph is the pulse transmitted from the ultrasound transducer 120 in response to the excitation of the transducer 120 with the four cycle 286 ns period square wave.

Figure 8B:
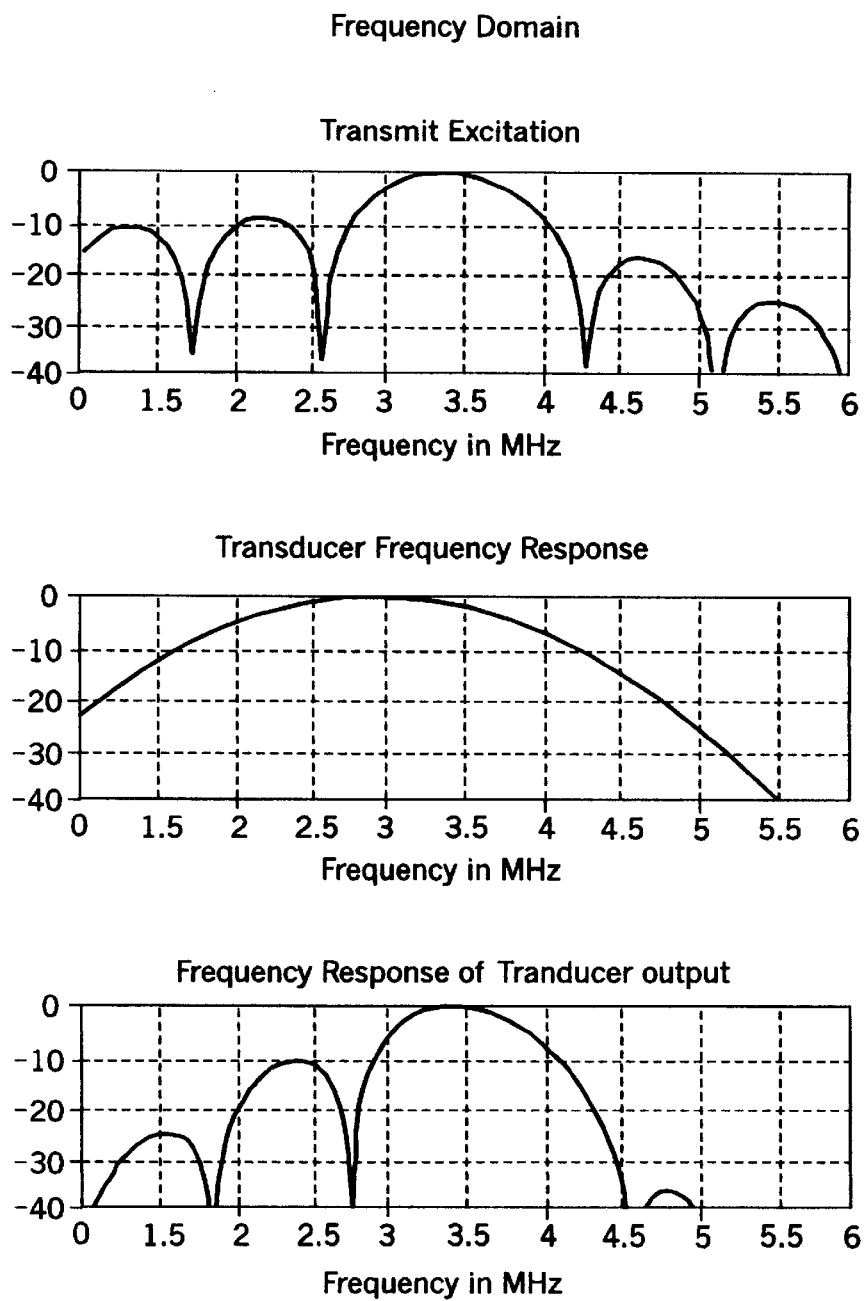
FIG. 8B is a series of graphs that illustrate the exemplary graphs of FIG. 8A in the frequency domain.

FIG. 8B is a series of graphs that illustrate the exemplary graphs of FIG. 8A in the frequency domain. The top graph illustrates the frequency content of the four cycle, 286 ns period, 50% duty cycle square wave. The middle graph illustrates the frequency response of the ultrasound transducer 120. The bottom graph illustrates the frequency content of the generated 3.5 MHz transmit ultrasound beam. In particular, the 3.5 MHz transmit ultrasound beam includes energy at 2.5 MHz which is 11 dB below the level found at 3.5 MHz. This means that using a 2.5 MHz bandpass filter on the 3.5 MHz transmit ultrasound beam may lessen the interference by 11 dB.

As more cycles are added to respective excitation signals, the frequency diversity between the 3.5 MHz and 2.5 MHz transmit ultrasound beams may increase. An increase in frequency diversity may provide for improved filtering to separate the respective receive ultrasound beams. The axial resolution of the respective transmit ultrasound beam may, however, decrease as the number of cycles increases. It is believed, however, that an excitation signal including four cycles as illustrated in FIGS. 7A and 8A will provide adequate frequency diversity while maintaining acceptable axial resolution.

The frequencies described herein are selected based on the bandwidth of the ultrasound transducer used to generate the transmit ultrasound beams and receive the reflected pressure waves. As shown in the middle graphs of FIGS. 7B and 8B, the selected excitation frequencies (2.5 MHz and 3.5 MHz respectively) may generate responses from the ultrasound transducer which are attenuated less than 6 dB. Otherwise the ultrasound transducer may generate transmit ultrasound beams of lower energy.

As described above, the receive ultrasound beams may be separated by a bandpass filter. The bandpass filter can be an analog or digital filter, such as a Finite Impulse Response Filter (FIR). It will be understood by those of skill in the art that other filters may be used to separate the receive ultrasound beams.

Figure 9:
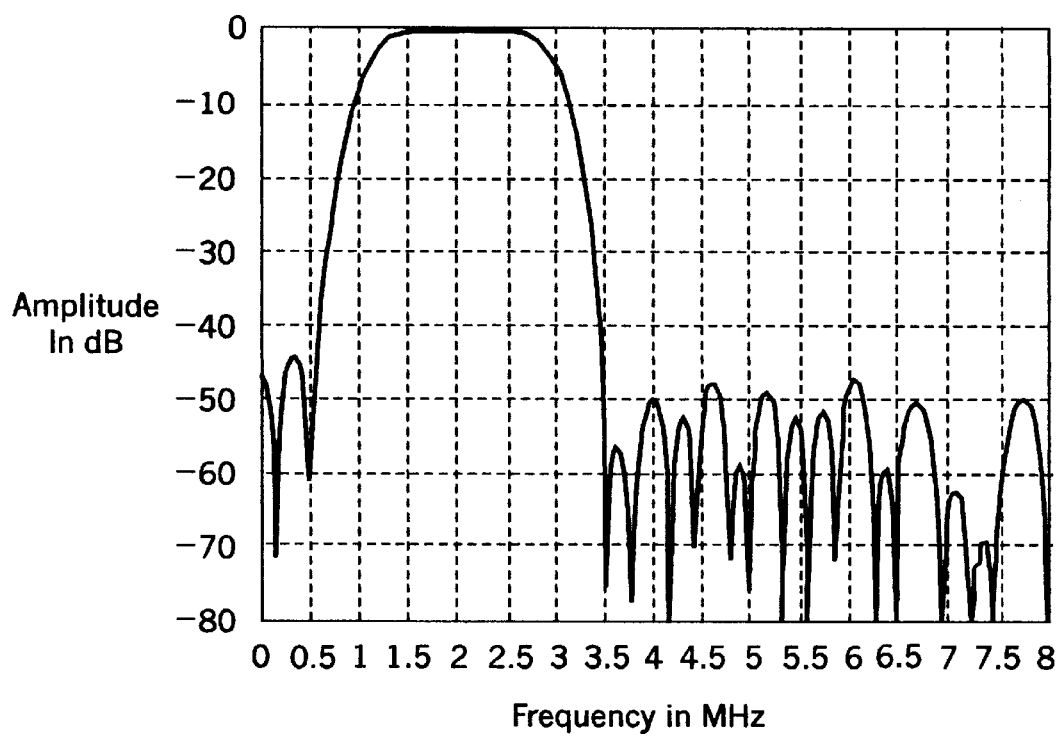
FIG. 9 is a graph that illustrates the frequency response of a digital filter that may be used to filter a 2.5 MHz receive ultrasound beam according to an embodiment of the present invention.

FIG. 9 is a graph that illustrates the frequency response of a digital FIR filter which may be used to filter a 2.5 MHz receive ultrasound beam according to the present invention. In particular, the filter of FIG. 9 is a 360 tap, 2.0 MHz center frequency bandpass filter designed to pass the electrical signals generated by the 2.5 MHz transmit ultrasound beams and reject the electrical signals generated by the 3.5 MHz transmit ultrasound beams.

Figure 10:
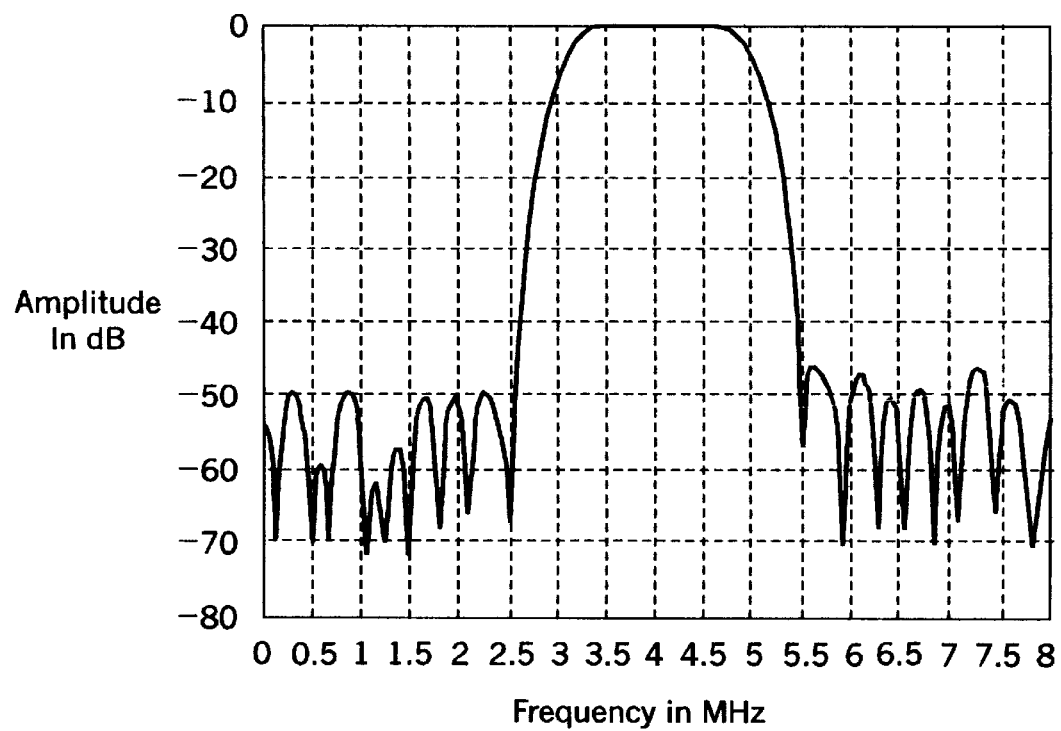
FIG. 10 is a graph that illustrates the frequency response of a digital filter that may be used to filter a 3.5 MHz receive ultrasound beam according to an embodiment of the present invention.

FIG. 10 is a graph that illustrates the frequency response of a filter which may be used to filter a 3.5 MHz receive ultrasound beam according to the present invention. In particular, the filter of FIG. 10 is a 360 tap, 4.0 MHz center frequency bandpass filter designed to pass the electrical signals generated by the 3.5 MHz transmit ultrasound beams and reject the electrical signals generated by the 2.5 MHz transmit ultrasound beams.

Figure 11:
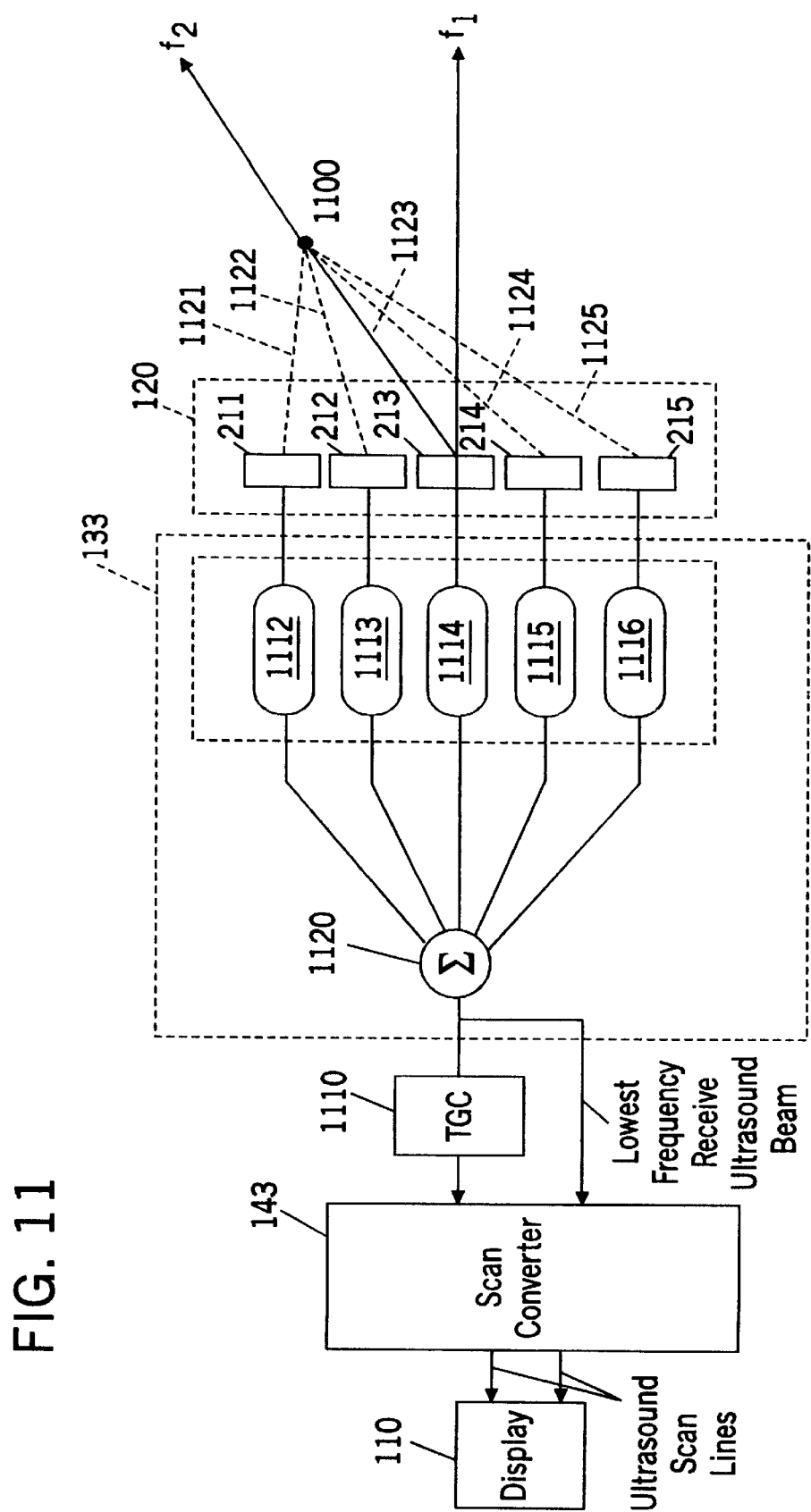
FIG. 11 is a block diagram of a post-summation time gain control circuit according to an embodiment of the present invention.

FIG. 11 is a block diagram of a post summation Time Gain Control circuit according to an embodiment of the present invention. Transmit ultrasound beams generated at higher frequencies may be attenuated more than transmit ultrasound beams generated at lower frequencies due to the physical properties of the tissue in which the transmit ultrasound beam propagates. The frequency dependent attenuation of a transmit ultrasound beam may be expressed as:

$$P(L) = e^{(-\alpha f L)} \quad (5)$$

where L is the distance traveled in region 140, α is 0.5 dB/(MHz cm), and f is the frequency of the transmit ultrasound beam. For an L of 300 mm, a frequency of 2.5 MHz, and α=0.5, the attenuation is 37.5 dB, while for a L of 300 mm, a frequency of 3.5 MHz, and α=0.5, the attenuation is 52.5 dB. In other words, the 3.5 MHz transmit ultrasound beam may be attenuated 15 dB more than the 2.5 MHz transmit ultrasound beam. The attenuation of the 3.5 MHz transmit ultrasound beam may create ultrasound scan lines that appear dim compared to ultrasound scan lines created by the 2.5 MHz transmit ultrasound beam.

Therefore, according to the embodiment of the present invention illustrated in FIG. 11, the reflected pressure waves corresponding to the higher frequency transmit ultrasound beam are processed using a post summation Time Gain Control (TGC). In particular, the reflected pressure waves are received by the ultrasound transducer elements 211, 212, 213, 214, 215 and phase shifted by delay lines 1112–1115 according to the respective distances (1121, 1122, 1123, 1124, 1125) between the ultrasound transducer elements and a focus point 1100 in the region 140. The gain of the electrical signals corresponding to the lowest frequency reflected pressure waves is adjusted according to techniques known to those having skill in the art. The lowest frequency receive ultrasound beam is formed by the delay lines 1112–1116 which align the electrical signals generated by the transducer elements 211–215 to form the lowest frequency received transmit ultrasound beam.

The higher frequency transmit ultrasound beam is processed by a post summation TGC 1110. In particular, the higher frequency transmit ultrasound beam is tracked, wherein the electrical signals generated by the ultrasound transducer elements 211–215 are shifted by the delay lines 1112–1116 to bring the electrical signals in-phase. The in-phase electrical signals are summed by a summation circuit 1120 to provide the higher frequency receive ultrasound beam. The TGC 1110 adjusts the amplitude of the summed higher frequency receive ultrasound beam to compensate for the attenuation of the higher frequency transmit ultrasound beam and thereby allow a reduction in the brightness difference between lower and higher frequency ultrasound scan lines. Accordingly, a display may be provided wherein the ultrasound scan lines generated at different frequencies have substantially uniform brightness on a display screen.

Figure 12:
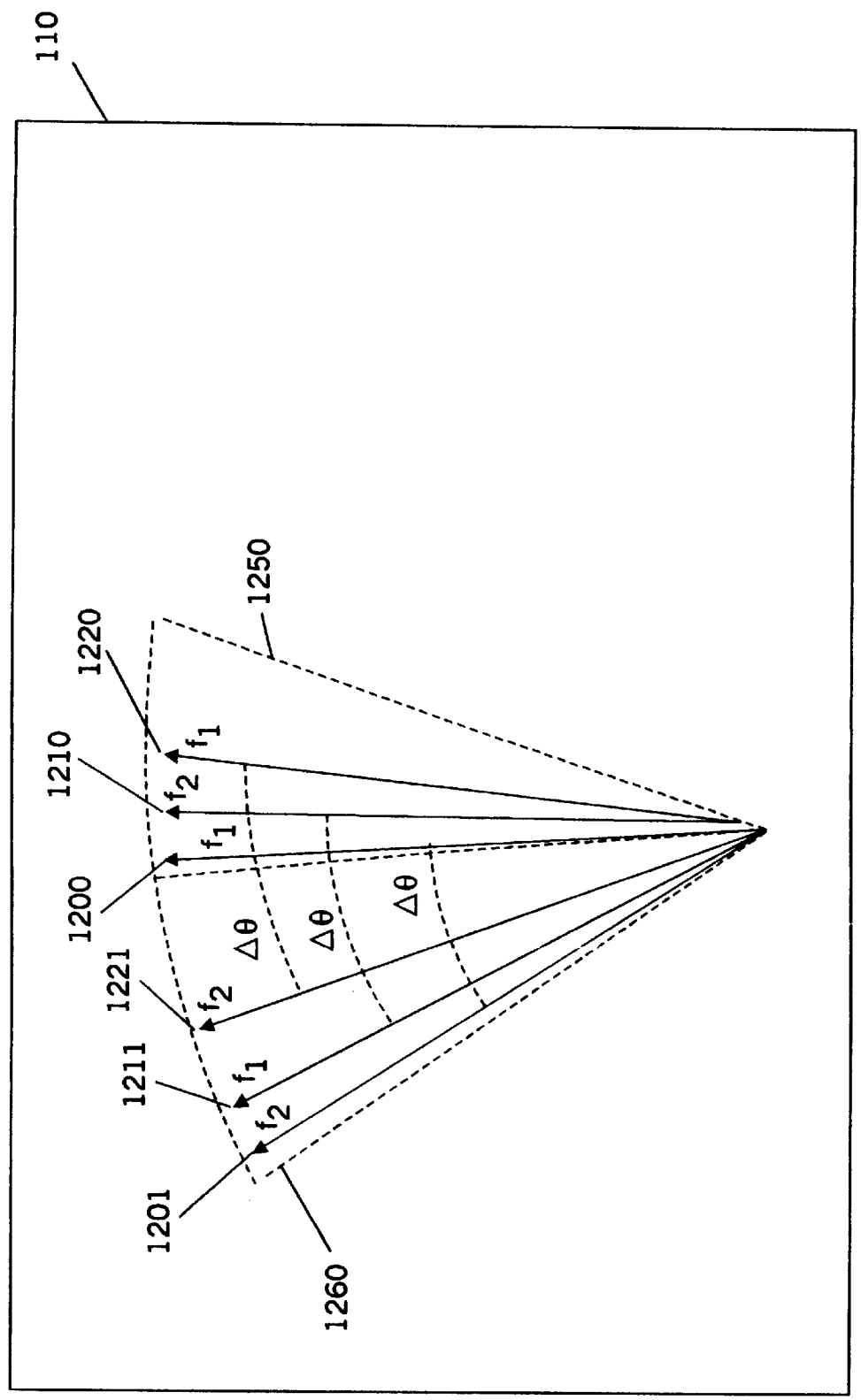
FIG. 12 is a diagram of a line-by-line frequency interlaced display of ultrasound scan lines according to an embodiment of the present invention.

FIG. 12 is a diagram of a line-by-line frequency interlaced display of spatially and spectrally separated transmit ultrasound beams according to an embodiment of the present invention. The line-by-line frequency interlaced display may reduce the effect of frequency dependent attenuation in the region. The line-by-line frequency interlacing may also reduce a difference in speckle size due to the different frequencies.

As illustrated in FIG. 12, adjacent ultrasound scan lines of the display 110 are generated with different frequencies. For example, a first ultrasound scan line 1200 in a first display sector 1250 is generated from a 2.5 MHz transmit ultrasound beam steered at −15° relative to the face of the ultrasound transducer 120, while a first ultrasound scan line 1201 in a second display sector 1260 is generated using a 3.5 MHz transmit ultrasound beam steered at −30° relative to the face of the ultrasound transducer 120. The second ultrasound scan line 1210 in the first display sector 1250 is generated using a 3.5 MHz transmit ultrasound beam steered at −14.5° relative to the face of the ultrasound transducer 120, while the second ultrasound beam 1211 in the second display sector 1260 is generated using a 2.5 MHz transmit ultrasound beam is steered at −29.5° relative to the face of the ultrasound transducer 120.

A third ultrasound scan line 1220 in the first display sector 1250 is generated using a 2.5 MHz transmit ultrasound beam steered at −14° relative to the face of the ultrasound transducer 120 while a third ultrasound scan line 1221 in the second display sector 1260 is generated from a 3.5 MHz transmit ultrasound beam steered at −29° relative to the face of the ultrasound transducer 120. This produces a display wherein adjacent ultrasound scan lines on the display 110 are generated by transmit ultrasound beams having different frequencies.

As will be appreciated by one of skill in the art, the present invention may be embodied as a method, data processing system or computer program product. Accordingly, the present invention may take the form of an entirely hardware embodiment, an entirely software embodiment or an embodiment combining software and hardware aspects. Furthermore, the present invention may take the form of a computer program product on a computer-readable storage medium having computer-readable program code means embodied in the medium. Any suitable computer readable medium may be utilized including, but not limited to, hard disks, CD-ROMs, optical storage devices, magnetic storage devices, and electronic storage devices.

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A method of scanning tissue in a body using transit ultrasound beams, the method comprising the step of generating a plurality of transmit ultrasound beams in a plurality of directions, wherein at least two of the plurality of transmit ultrasound beams are generated at a different associated frequency, wherein a time interval from a first start time of one of the plurality of transmit ultrasound beams to a second start time of another of the plurality of transmit ultrasound beams is less than a total time for one of the plurality of transmit ultrasound beams to propagate from an ultrasound transducer array to a maximum scan range in the region and a corresponding reflected pressure wave to propagate from the maximum scan range to the ultrasound transducer array.

2. The method of claim 1, wherein the step of generating comprises the step of generating a plurality of excitations, each including a plurality of associated signals, wherein each of the plurality of excitations produces a respective one of the plurality of transmit ultrasound beams.

3. The method of claim 1, wherein the step of generating comprises the steps of:

generating a first plurality of signals having an associated first frequency to cause an ultrasound transducer array to transmit a first transmit ultrasound beam at the first frequency in a first direction; and generating a second plurality of signals having an associated second frequency that is different than the first frequency to cause an ultrasound transducer array to transmit a second transmit ultrasound beam at the second frequency in a second direction.

4. The method of claim 3 further comprising the steps of:

tracking the first and second transmit ultrasound beams to provide respective first and second receive ultrasound beams; and filtering the first and second receive ultrasound beams to provide respective first and second ultrasound scan lines.

5. A method of scanning tissue in a body using transmit ultrasound beams, the method comprising the step of transmitting a plurality of transmit ultrasound beams in a plurality of directions in the body at a series of start times from an ultrasound transducer, each of the plurality of transmit ultrasound beams being transmitted at one of a plurality of frequencies, wherein a time interval from a first start time of one of the plurality of transmit ultrasound beams to a second start time of another of the plurality of transmit ultrasound beams is less than a total time for one of the plurality of transmit ultrasound beams to propagate to a maximum scan range in the region and a corresponding reflected pressure wave to propagate from the maximum scan range to the ultrasound transducer.

6. The method of claim 5 further comprising steps of:

tracking the plurality of transmit ultrasound beams to provide a respective plurality of receive ultrasound beams;

filtering the plurality of receive ultrasound beams to provide a respective plurality of ultrasound scan lines; and displaying the plurality of ultrasound scan lines.

7. The method of claim 5, wherein the step of transmitting comprises the steps of:

transmitting a first transmit ultrasound beam at a first frequency in a first direction from the ultrasound transducer at the first start time; and then transmitting a second transmit ultrasound beam at a second frequency, that is different than the first frequency, in a second direction at a second start time that follows the first start time, wherein the time interval between the first start time and the second start time is less than the total time.

8. The method of claim 7, wherein the step of tracking comprises the steps of:

tracking the first transmit ultrasound beam to form a first receive ultrasound beam; and then adjusting a gain of the first receive ultrasound beam.

9. The method of claim 8, wherein the step of transmitting the second transmit ultrasound beam comprises the step of transmitting the second transmit ultrasound beam at a lower frequency than the first transmit ultrasound beam.

10. A method according to claim 5, wherein the plurality of frequencies are selected to reduce interference between reflected pressure waves generated within the maximum scan range.

11. A method for reducing speckle in ultrasound images of tissue in a body comprising the steps of:

transmitting a first transmit ultrasound beam at a first frequency in a first direction and a second transmit ultrasound beam at a second frequency in a second direction, the first and second directions defining a separation angle therebetween, wherein a time interval from a first start time of the first transmit ultrasound beam to a second start time of the second transmit ultrasound beam is less than a total time for the first transmit ultrasound beam to propagate from an ultrasound transducer array to a maximum scan range in the region and a corresponding reflected pressure wave to propagate from the maximum scan range to the ultrasound transducer array; and transmitting a third transmit ultrasound beam at a third frequency in a third direction, substantially adjacent to the first direction, and a fourth transmit ultrasound beam at a fourth frequency in a fourth direction, substantially adjacent to the second direction, the third and fourth directions defining a separation angle therebetween, wherein the third and fourth transmit ultrasound beams are transmitted prior to expiration of the time interval.

12. The method of claim 11, wherein the first and fourth frequencies are equal and the second and third frequencies are equal and are different than the first and fourth frequencies, wherein the method further comprises the steps of:

tracking the first through fourth transmit ultrasound beams to provide respective first through fourth ultrasound scan lines;

displaying the first and third ultrasound scan lines adjacent to each other on a display; and displaying the second and fourth ultrasound scan lines adjacent to each other on the display to provide an image of substantially uniform brightness on the display.

13. The method of claim 12, wherein the step of transmitting comprises the steps of:

transmitting a first transmit ultrasound beam at a first frequency in a first direction in a first sector of the body; and transmitting a second ultrasound transmit beam at a second frequency in a second direction in the first sector of the body.

14. The method of claim 13, wherein the transmitting the second transmit ultrasound beam comprises the step of transmitting the second ultrasound transmit beam at the second frequency in the second direction in the first sector of the body adjacent to the first direction.

15. A method according to claim 11 further comprising:

tracking the first through fourth transmit ultrasound beams to provide respective first through fourth ultrasound scan lines;

displaying the first and third ultrasound scan lines in a first sector of a display; and displaying the second and fourth ultrasound scan lines in a second sector of the display, wherein the second sector is displaced from the first sector.

16. A system that scans tissue in a body using transmit ultrasound beams, the system comprising:

means for generating a first plurality of signals having an associated first frequency to cause an ultrasound transducer array to transmit a first transmit ultrasound beam at the first frequency in a first direction; and means for generating a second plurality of signals having an associated second frequency that is different than the first frequency to cause an ultrasound transducer array to transmit a second transmit ultrasound beam at the second frequency in a second direction, wherein a time interval from a first start time of the first transmit ultrasound beam to a second start time of the second transmit ultrasound beams is less than a total time for the first transmit ultrasound beam to propagate from the ultrasound transducer array to a maximum scan range in the region and a corresponding reflected pressure wave to propagate from the maximum scan range to the ultrasound transducer array.

17. The system of claim 16 further comprising:

means for tracking the first and second transmit ultrasound beams to provide respective first and second receive ultrasound beams; and means for filtering the first and second receive ultrasound beams to provide respective first and second ultrasound scan lines.

18. A system that scans tissue in a body using transmit ultrasound beams, the system comprising:

means for transmitting a first transmit ultrasound beam at a first frequency in a first direction from an ultrasound transducer at a first start time to a maximum scan range to produce a corresponding reflected pressure wave; and means for transmitting a second transmit ultrasound beam at a second frequency, that is different than the first frequency, in a second direction in the region at a second start time that follows the first start time, wherein a time interval between the first start time of one of the plurality of transmit ultrasound beams and the second start time of another of the plurality of transmit ultrasounds beams is less than a total time for one of the plurality of transmit ultrasound beams to propagate to the maximum scan range in the region and the corresponding reflected pressure wave to propagate from the maximum scan range to the ultrasound transducer.

19. The system of claim 18 further comprising:

means for tracking the first and second transmit ultrasound beams to provide a respective first and second receive ultrasound beams;

means for filtering the first and second receive ultrasound beams to provide a respective first and second ultrasound scan lines; and means for displaying the first and second receive ultrasound scan lines.

20. The system of claim 19, wherein the means for tracking comprises:

means for tracking the first transmit ultrasound beam to provide the first receive ultrasound beam; and means for applying a gain to the first receive ultrasound beam.

21. The system of claim 20, wherein the first transmit ultrasound beam is generated at a higher frequency than the second transmit ultrasound beam.

22. A system according to claim 18, wherein the first and second frequencies are selected to reduce interference between reflected pressure waves generated within the maximum scan range.

23. A system for reducing speckle in ultrasound images comprising:

means for transmitting a first transmit ultrasound beam at a first frequency in a first direction and a second transmit ultrasound beam at a second frequency in a second direction, the first and second directions defining a separation angle therebetween, wherein a time interval from a first start time of the first transmit ultrasound beam to a second start time of the second transmit ultrasound beams is less than a total time for the first transmit ultrasound beam to propagate from an ultrasound transducer array to a maximum scan range in the region and a corresponding reflected pressure wave to propagate from the maximum scan range to the ultrasound transducer array; and means for transmitting a third transmit ultrasound beam at a third frequency in a third direction, substantially adjacent to the first direction, and a fourth transmit ultrasound beam at a fourth frequency in a fourth direction, substantially adjacent to the second direction, the third and fourth directions defining a separation angle therebetween, wherein the third and fourth transmit ultrasound beams are transmitted prior to expiration of the time interval.

24. The system of claim 23, wherein the first and fourth frequencies are equal and the second and third frequencies are equal, and wherein the system further comprises:

means for tracking the first through fourth transmit ultrasound beams to provide respective first through fourth ultrasound scan lines;

means for displaying the first and third ultrasound scan lines adjacent to each other on a display; and means for displaying the second and fourth ultrasound scan lines adjacent to each other on the display to provide an image of substantially uniform brightness on the display.

25. A system according to claim 23 further comprising:

means for tracking the first through fourth transmit ultrasound beams to provide respective first through fourth ultrasound scan lines;

means for displaying the first and third ultrasound scan lines in a first sector of a display; and means for displaying the second and fourth ultrasound scan lines in a second sector of the display.

26. A method of scanning tissue in a body using transmit ultrasound beams, the method comprising the steps of:

transmitting a first transmit ultrasound beam at a first frequency in a first direction from an ultrasound transducer array at a first start time; and transmitting a second transmit ultrasound beam at a second frequency, that is different than the first frequency, in a second direction from the ultrasound transducer array at a second start time that follows the first start time, wherein the time interval between the first start time and the second start time is less than a total time for the first transmit ultrasound beam to propagate from the ultrasound transducer array to a maximum scan range in the region and a corresponding reflected pressure wave to propagate from the maximum scan range to the ultrasound transducer array, and wherein the first and second frequencies are selected to reduce interference between reflected pressure waves generated within the maximum scan range.

27. A method for reducing speckle in ultrasound images of tissue in a body comprising the steps of:

transmitting a first transmit ultrasound beam at a first frequency in a first direction; and transmitting a second transmit ultrasound beam at a second frequency in a second direction, the first and second directions defining a separation angle therebetween in a range between about 10 and 30 about degrees, wherein a time interval from a first start time of the first transmit ultrasound beam to a second start time of the second transmit ultrasound beam is less than a total time for the first transmit ultrasound beam to propagate from an ultrasound transducer array to a maximum scan range in the region and a corresponding reflected pressure wave to propagate from the maximum scan range to the ultrasound transducer array.

28. A method according to claim 27, wherein the separation angle is in a range between about 10 and 20 about degrees.

* * * * *